US009101315B2

(12) United States Patent
Winfree et al.

(10) Patent No.: US 9,101,315 B2
(45) Date of Patent: Aug. 11, 2015

(54) CANNULA SYSTEM

(75) Inventors: Alan Winfree, Franklin, TN (US);
Robert Henry, Nashville, TN (US)

(73) Assignee: Specialty Care, Inc., Nashville, TN (US)

( * ) Notice: Subject to any disclaimer, the term of this patent is extended or adjusted under 35 U.S.C. 154(b) by 791 days.

(21) Appl. No.: 13/294,493

(22) Filed: Nov. 11, 2011

(65) Prior Publication Data

US 2012/0123216 A1    May 17, 2012

Related U.S. Application Data

(63) Continuation of application No. 61/412,553, filed on Nov. 11, 2010.

(51) Int. Cl.
*A61B 17/34* (2006.01)
*A61B 1/32* (2006.01)
*A61B 1/00* (2006.01)

(52) U.S. Cl.
CPC ............... *A61B 1/32* (2013.01); *A61B 1/00071* (2013.01); *A61B 17/3415* (2013.01); *A61B 17/3462* (2013.01); *A61B 17/3498* (2013.01); *A61B 17/3474* (2013.01); *A61B 2017/3484* (2013.01)

(58) Field of Classification Search
CPC .......... A61B 17/3415; A61B 17/3462; A61B 17/3498; A61B 17/3474; A61B 1/32; A61B 1/00071; A61B 2017/3484
USPC .................... 600/204, 205, 206, 208; 604/264
See application file for complete search history.

(56) References Cited

U.S. PATENT DOCUMENTS

| 5,242,412 A | 9/1993 | Blake, III |
| 5,256,149 A | 10/1993 | Banik et al. |
| 5,334,150 A | 8/1994 | Kaali |

(Continued)

FOREIGN PATENT DOCUMENTS

| DE | 10333956 | 2/2005 |
| EP | 0665029 | 1/1995 |

(Continued)

OTHER PUBLICATIONS

English Abstract of DE10333956, Feb. 17, 2005.

(Continued)

*Primary Examiner* — Jerry Cumberledge
*Assistant Examiner* — Nicholas Plionis
(74) *Attorney, Agent, or Firm* — Preston Smirman; Smirman IP Law, PLLC

(57) ABSTRACT

A cannula system is described. The cannula system may be formed of biocompatible materials that are suitable to be sterilized. Accordingly, the cannula system may be reusable for a relatively large number of surgical procedures assuming conventional sterilization techniques are employed after each surgical procedure. Additionally, the cannula system may be provided with an internal valve system disposed in a port portion thereof wherein the valve system may be operable to receive the trocar there through, as well as maintaining insufflation of the body cavity. Furthermore, the cannula system may be provided with a plurality of rib members formed on an external surface of the cannula shaft, wherein the rib members may engage the tissues adjacent the incision, thus maintaining the position of the cannula shaft and reducing and/or lessening relative movement of the cannula shaft.

19 Claims, 28 Drawing Sheets

(56) References Cited

U.S. PATENT DOCUMENTS

| | | | |
|---|---|---|---|
| 5,364,372 | A | 11/1994 | Danks et al. |
| 5,366,445 | A | 11/1994 | Haber et al. |
| 5,376,076 | A | 12/1994 | Kaali |
| 5,380,291 | A | 1/1995 | Kaali |
| 5,385,572 | A | 1/1995 | Nobles et al. |
| 5,387,196 | A | 2/1995 | Green et al. |
| 5,387,197 | A | 2/1995 | Smith et al. |
| 5,441,041 | A | 8/1995 | Sauer et al. |
| 5,449,370 | A | 9/1995 | Vaitekunas |
| 5,467,762 | A | 11/1995 | Sauer et al. |
| 5,499,625 | A | 3/1996 | Frass et al. |
| 5,545,150 | A | 8/1996 | Danks et al. |
| 5,569,160 | A | 10/1996 | Sauer et al. |
| 5,569,291 | A | 10/1996 | Privitera et al. |
| 5,569,292 | A | 10/1996 | Scwemberger et al. |
| 5,591,192 | A | 1/1997 | Privitera et al. |
| 5,603,702 | A | 2/1997 | Smith et al. |
| 5,607,440 | A | 3/1997 | Danks et al. |
| 5,620,456 | A | 4/1997 | Sauer et al. |
| 5,658,236 | A | 8/1997 | Sauer et al. |
| 5,697,913 | A | 12/1997 | Sierocuk et al. |
| 5,709,671 | A | 1/1998 | Stephens et al. |
| 5,738,628 | A | 4/1998 | Sierocuk et al. |
| 5,797,943 | A | 8/1998 | Danks et al. |
| 5,817,061 | A | 10/1998 | Goodwin et al. |
| 5,860,996 | A | 1/1999 | Urban et al. |
| 5,868,714 | A | 2/1999 | Danks |
| 5,895,377 | A | 4/1999 | Smith et al. |
| 5,904,699 | A | 5/1999 | Schwemberger et al. |
| 5,916,232 | A | 6/1999 | Hart |
| 5,957,888 | A | 9/1999 | Hinchliffe |
| 5,957,947 | A | 9/1999 | Wattiez et al. |
| 5,980,493 | A | 11/1999 | Smith et al. |
| 5,984,908 | A | 11/1999 | Davis et al. |
| 6,017,356 | A | 1/2000 | Frederick et al. |
| 6,063,099 | A | 5/2000 | Danks et al. |
| 6,228,061 | B1 | 5/2001 | Flatland et al. |
| 6,319,266 | B1 | 11/2001 | Stellon et al. |
| 6,371,967 | B1 | 4/2002 | Long et al. |
| 6,656,198 | B2 | 12/2003 | Tsonton et al. |
| 6,666,846 | B1 | 12/2003 | Turovskiy et al. |
| 6,685,630 | B2 | 2/2004 | Sauer et al. |
| 6,702,787 | B2 | 3/2004 | Racenet et al. |
| 6,740,064 | B1 * | 5/2004 | Sorrentino et al. ........... 604/264 |
| 6,923,783 | B2 | 8/2005 | Pasqualucci |
| 7,025,747 | B2 | 4/2006 | Smith |
| D542,918 | S | 5/2007 | Albrecht et al. |
| 7,320,694 | B2 | 1/2008 | O'Heeron |
| 7,322,933 | B2 | 1/2008 | Sauer et al. |
| 7,367,960 | B2 | 5/2008 | Stellon et al. |
| 7,470,230 | B2 | 12/2008 | Smith et al. |
| 7,559,918 | B2 | 7/2009 | Pasqualucci |
| 7,585,288 | B2 | 9/2009 | Haberland et al. |
| 7,597,701 | B2 | 10/2009 | Hueil et al. |
| 7,637,896 | B2 | 12/2009 | Voegele et al. |
| 7,686,823 | B2 | 3/2010 | Pingleton et al. |
| 7,722,570 | B2 | 5/2010 | Almond et al. |
| 7,758,603 | B2 | 7/2010 | Taylor et al. |
| 7,794,644 | B2 | 9/2010 | Taylor et al. |
| 7,824,327 | B2 | 11/2010 | Smith |
| 7,918,826 | B2 | 4/2011 | Armstrong et al. |
| 7,947,058 | B2 | 5/2011 | Kahle et al. |
| 7,967,791 | B2 | 6/2011 | Franer et al. |
| 2002/0072713 | A1 | 6/2002 | Almond et al. |
| 2005/0070850 | A1 | 3/2005 | Albrecht |
| 2005/0070947 | A1 | 3/2005 | Franer et al. |
| 2005/0149096 | A1 | 7/2005 | Hilal et al. |
| 2006/0173479 | A1 | 8/2006 | Smith |
| 2006/0253077 | A1 * | 11/2006 | Smith ..................... 604/167.06 |
| 2006/0264992 | A1 | 11/2006 | Franer et al. |
| 2007/0010842 | A1 | 1/2007 | Popov |
| 2007/0088277 | A1 | 4/2007 | McGinley et al. |
| 2007/0093851 | A1 | 4/2007 | Moran et al. |
| 2007/0185453 | A1 | 8/2007 | Michael et al. |
| 2007/0260273 | A1 | 11/2007 | Cropper et al. |
| 2007/0260275 | A1 | 11/2007 | Ahlberg et al. |
| 2007/0282266 | A1 * | 12/2007 | Davidson ................. 604/164.01 |
| 2008/0051735 | A1 | 2/2008 | Measamer et al. |
| 2008/0086074 | A1 | 4/2008 | Taylor et al. |
| 2008/0294184 | A1 | 11/2008 | Smith |
| 2009/0076323 | A1 | 3/2009 | Smith et al. |
| 2009/0093833 | A1 | 4/2009 | Smith |
| 2009/0270817 | A1 | 10/2009 | Moreno et al. |
| 2009/0281376 | A1 | 11/2009 | Acosta et al. |
| 2009/0281386 | A1 | 11/2009 | Acosta et al. |
| 2009/0281498 | A1 | 11/2009 | Acosta et al. |
| 2009/0281500 | A1 | 11/2009 | Acosta et al. |
| 2010/0016664 | A1 | 1/2010 | Viola |
| 2010/0022959 | A1 | 1/2010 | Moran et al. |
| 2010/0081988 | A1 | 4/2010 | Kahle et al. |
| 2010/0137895 | A1 | 6/2010 | Smith |

FOREIGN PATENT DOCUMENTS

| | | |
|---|---|---|
| EP | 1707132 | 10/2006 |
| JP | 7250810 | 10/1995 |

OTHER PUBLICATIONS

English Abstract of JP7250810, Oct. 3, 1995.

* cited by examiner

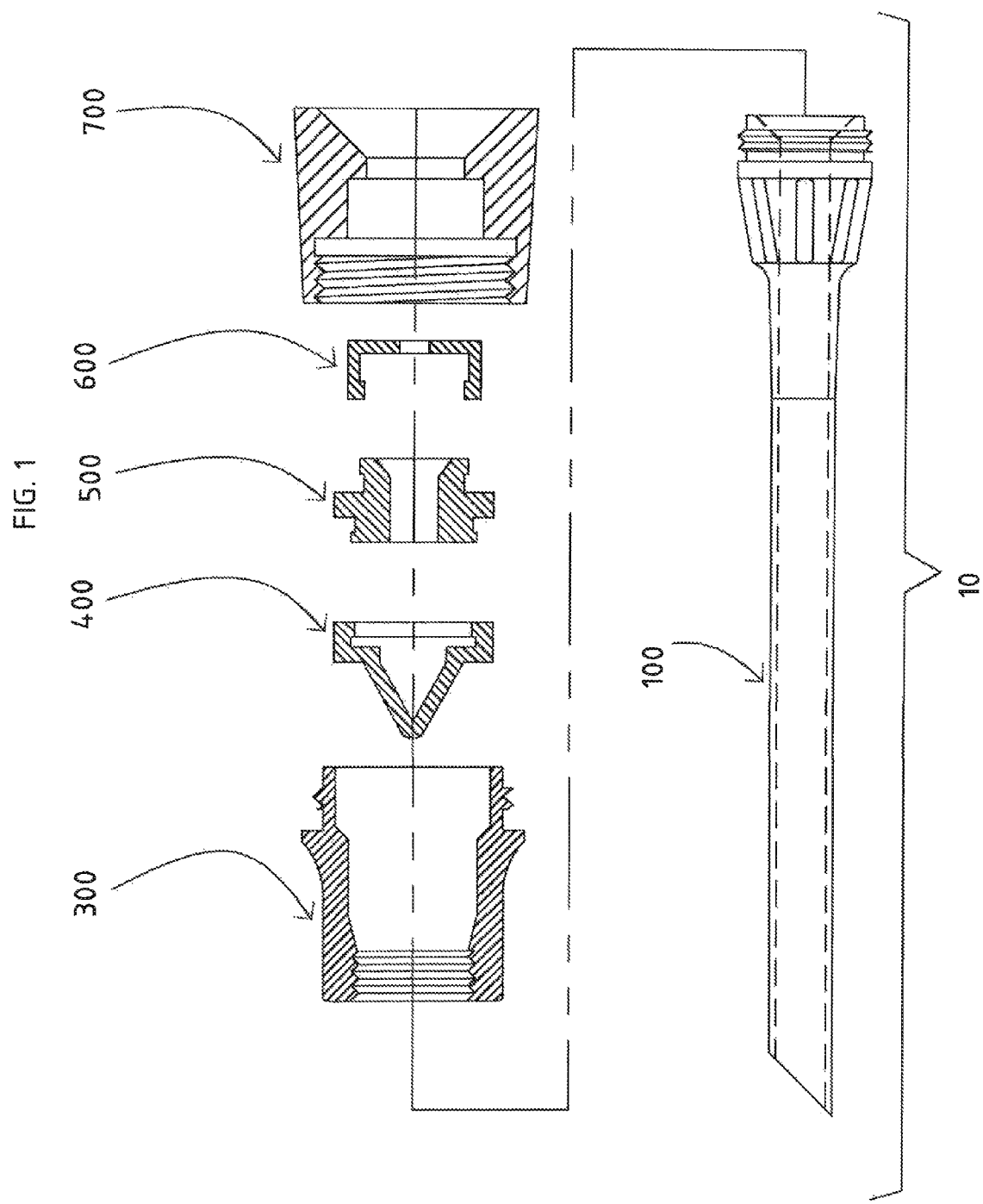

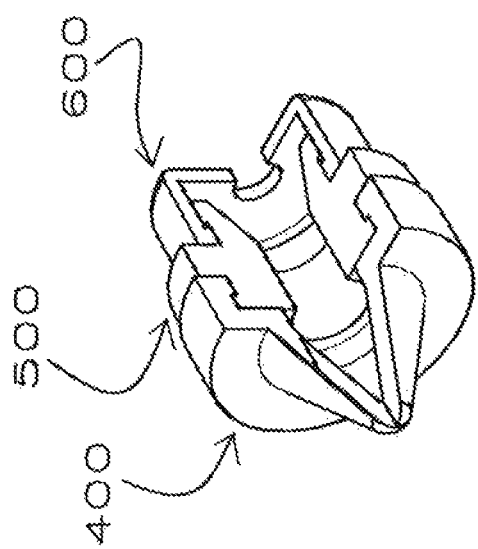

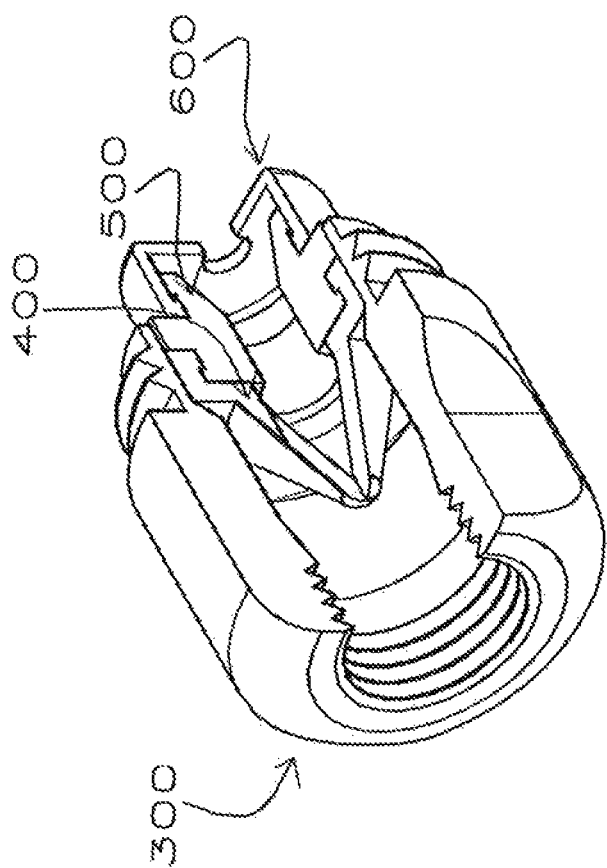

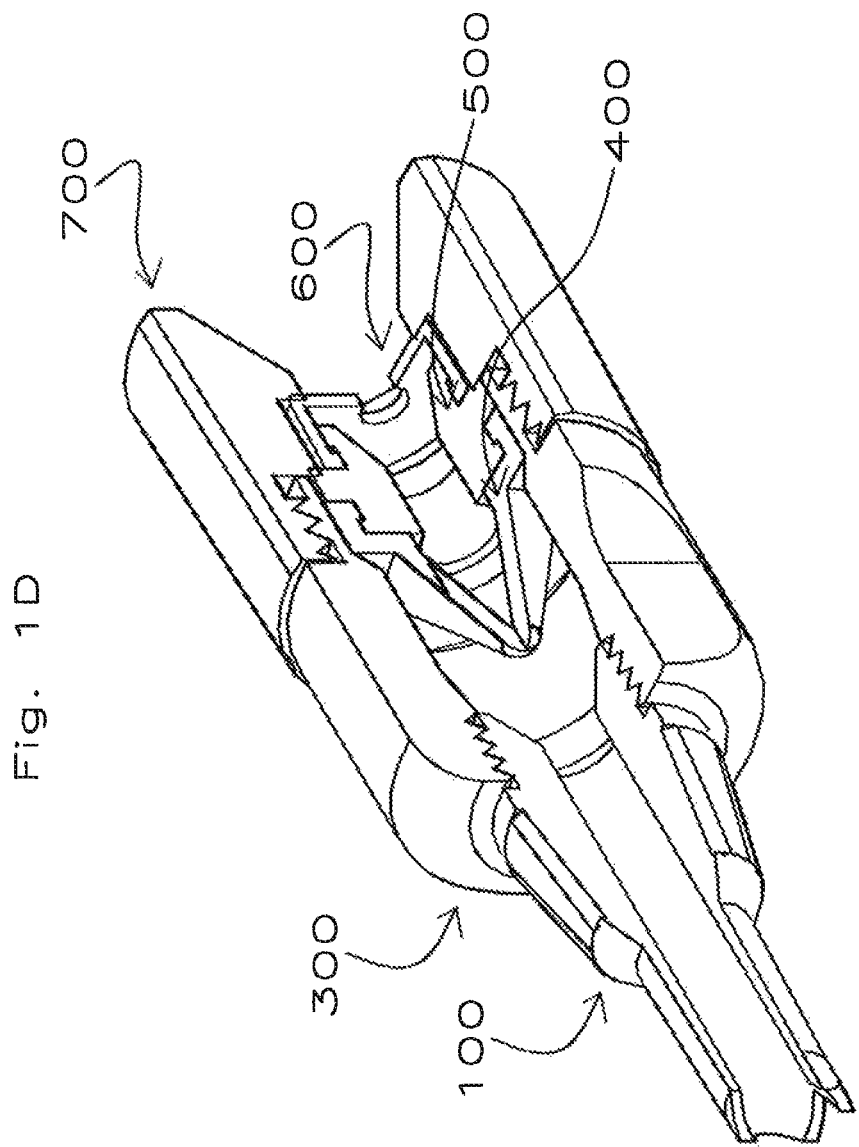

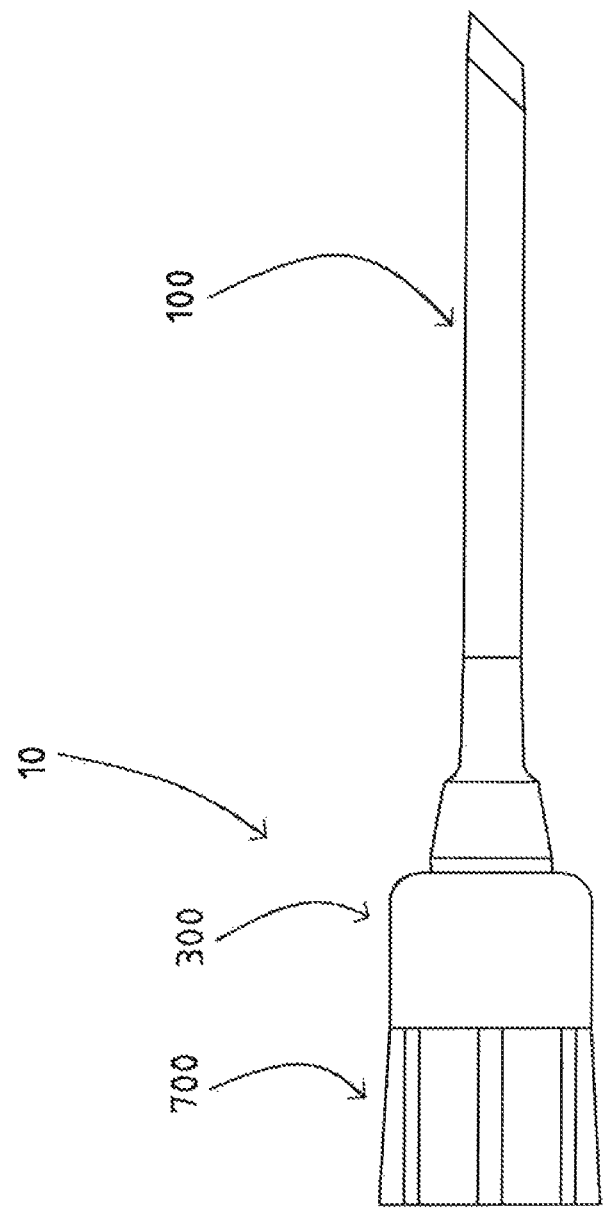

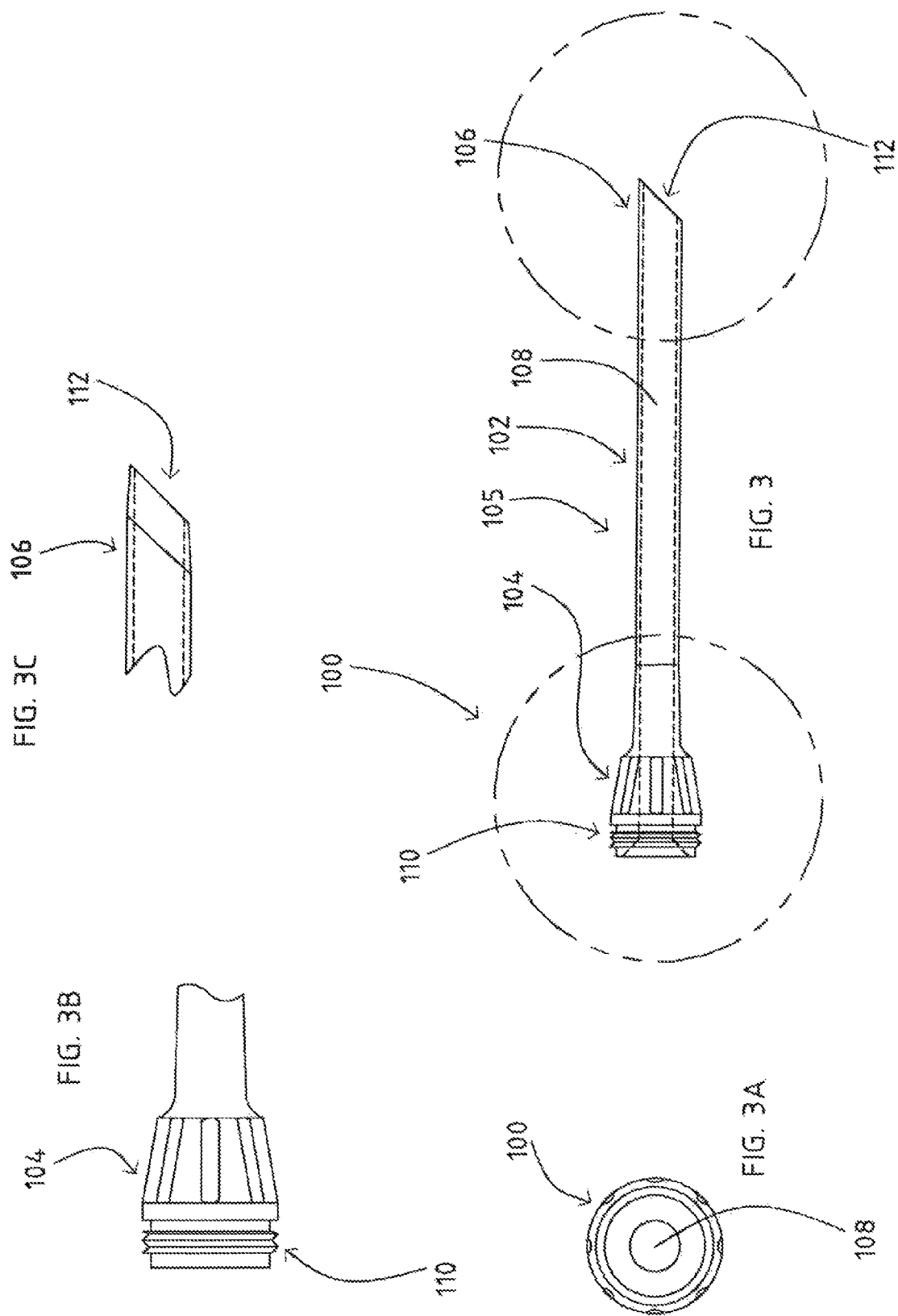

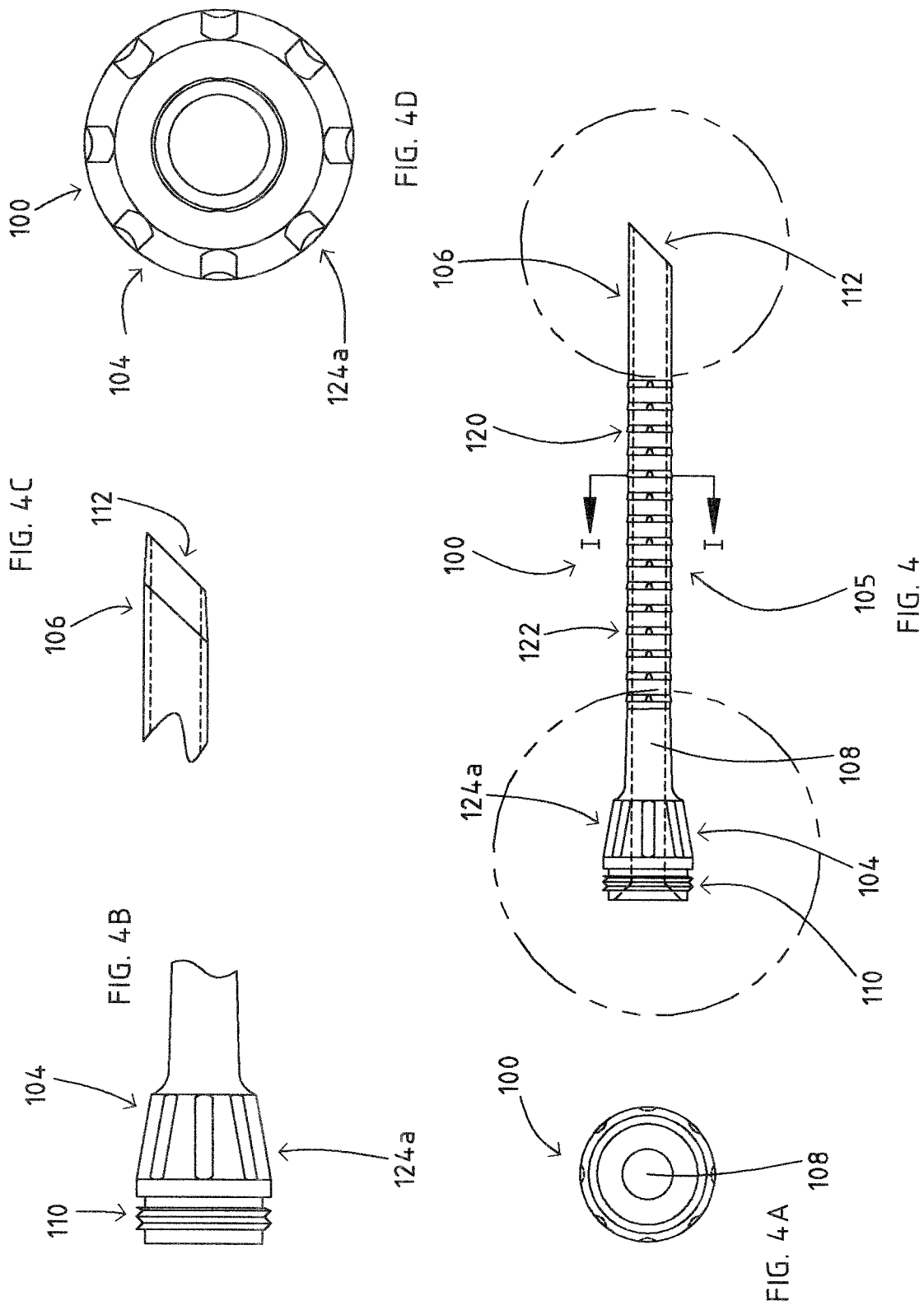

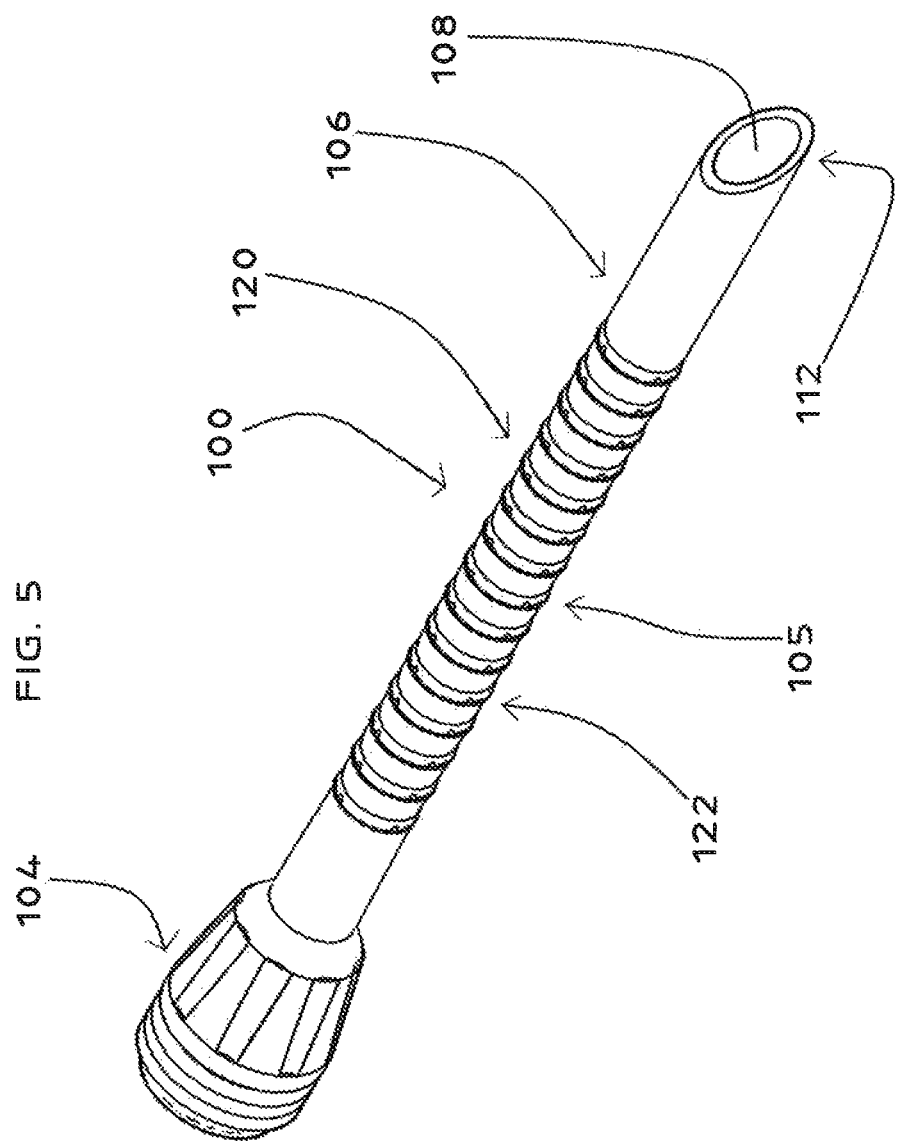

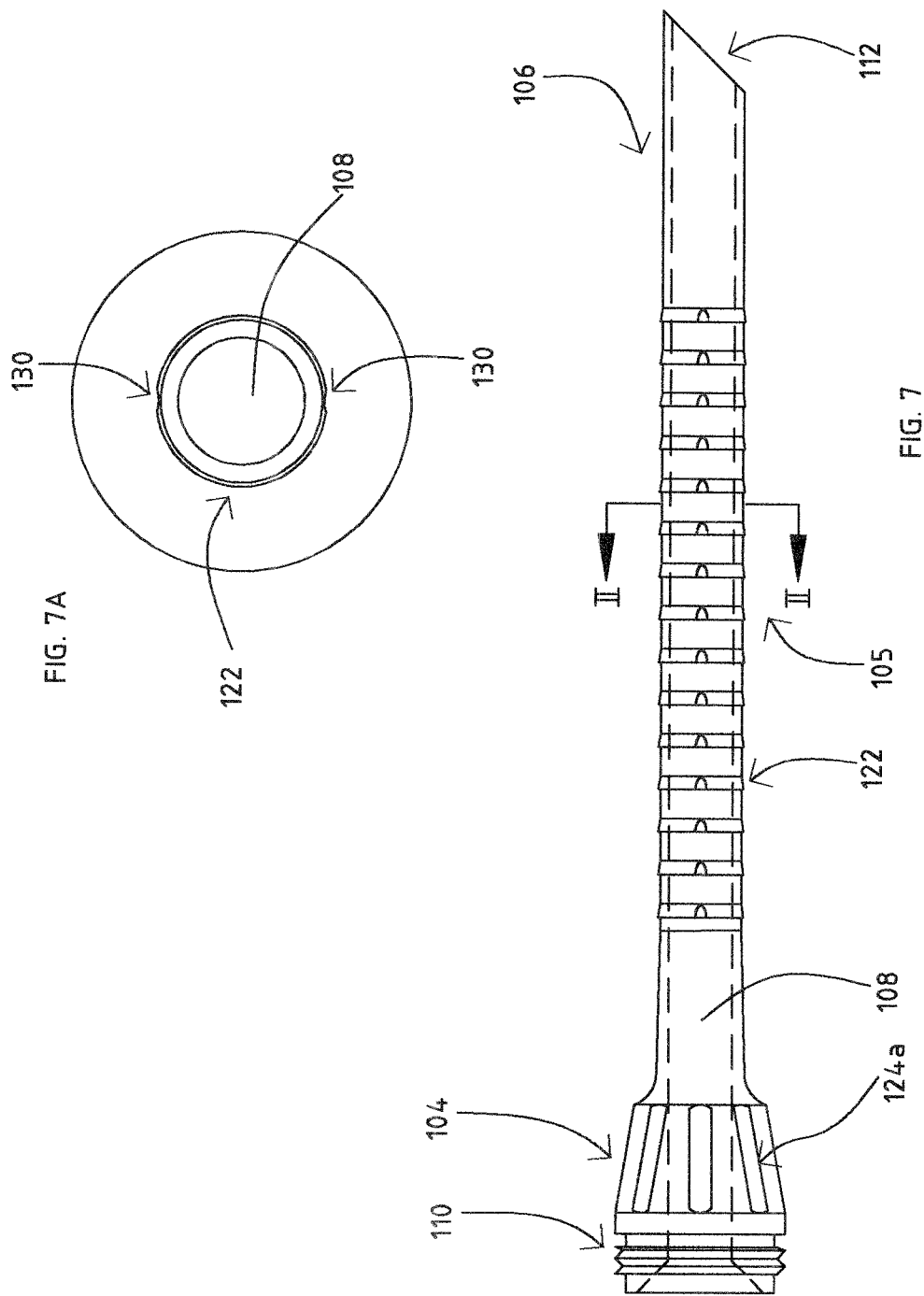

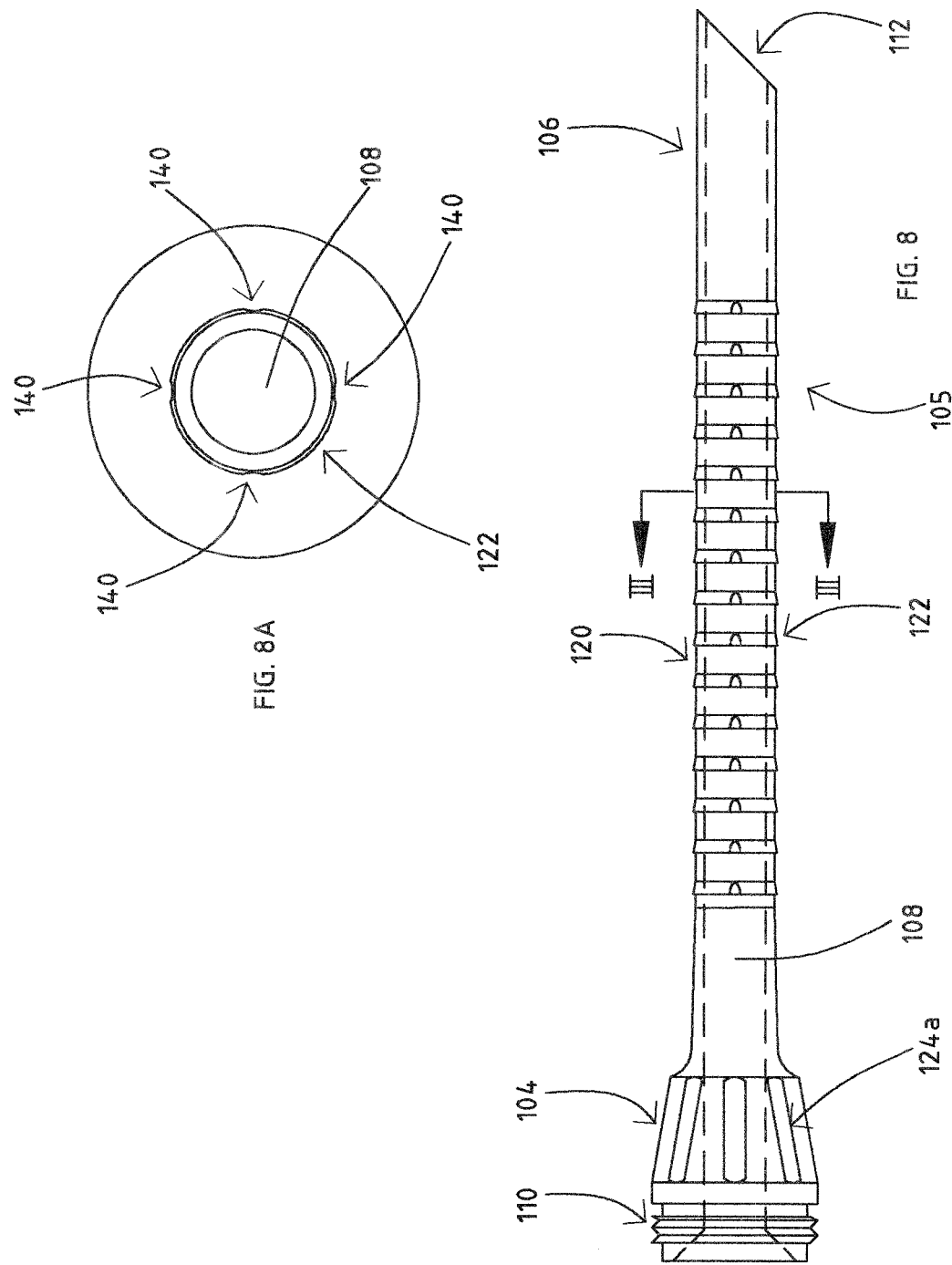

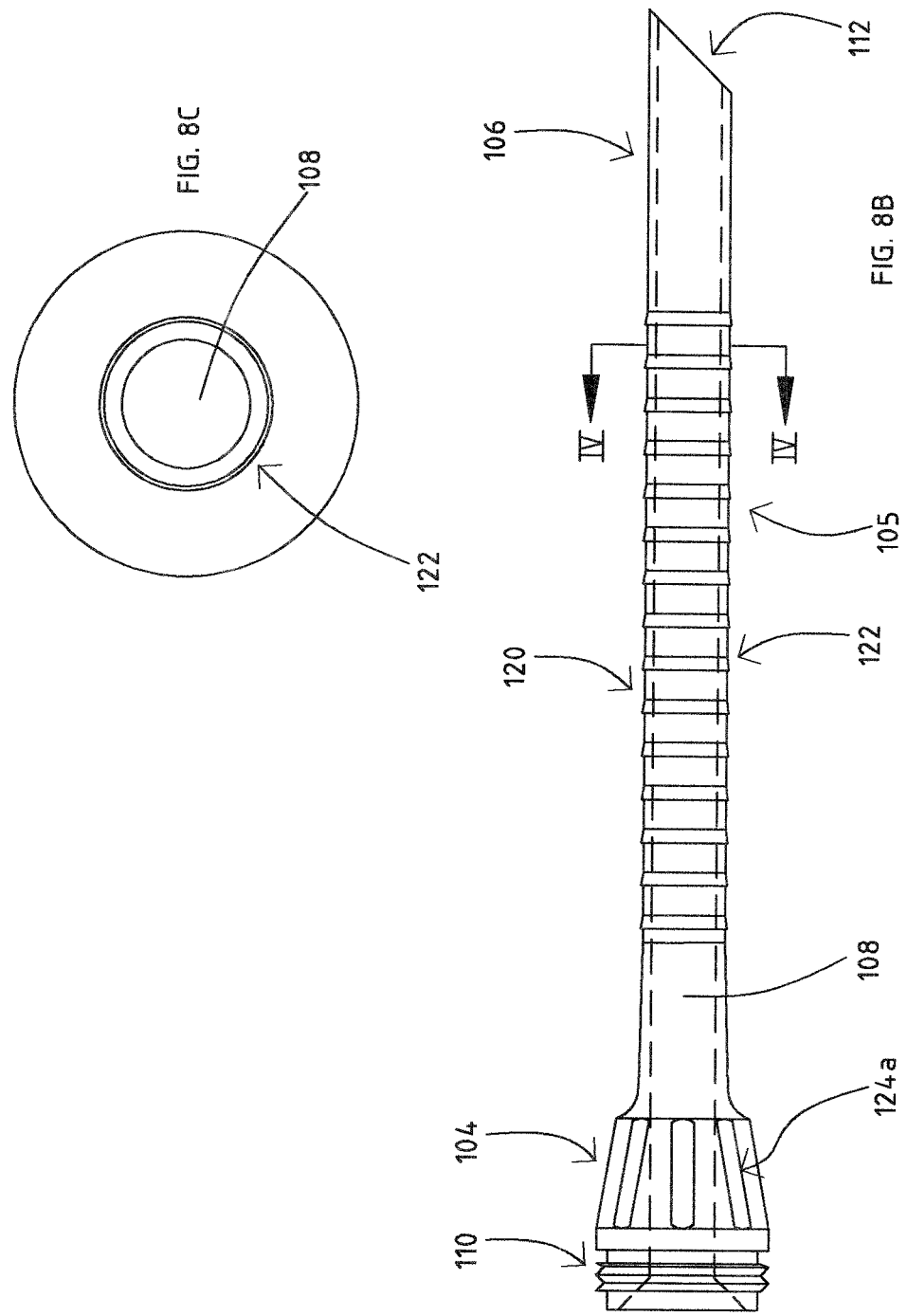

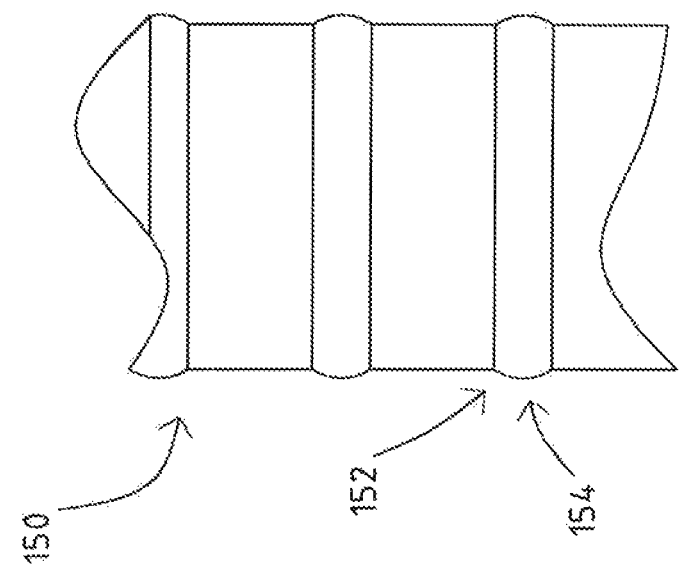
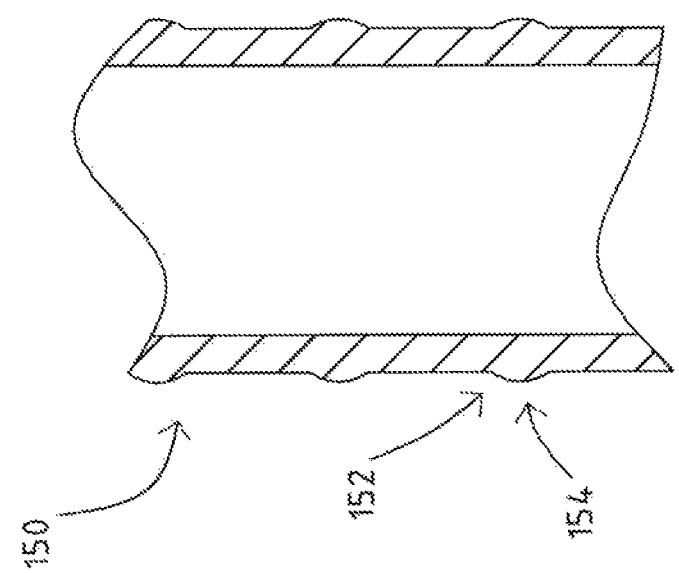

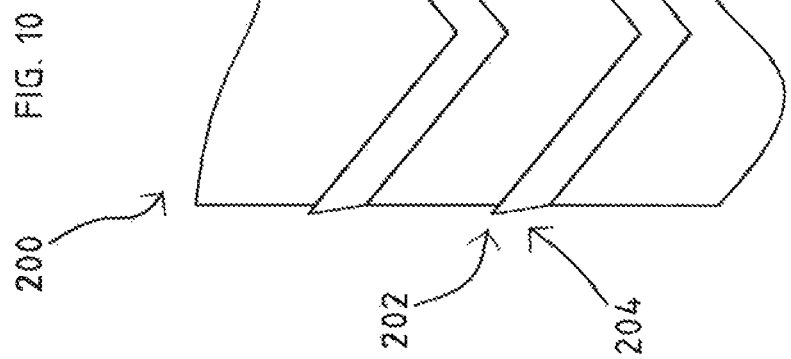
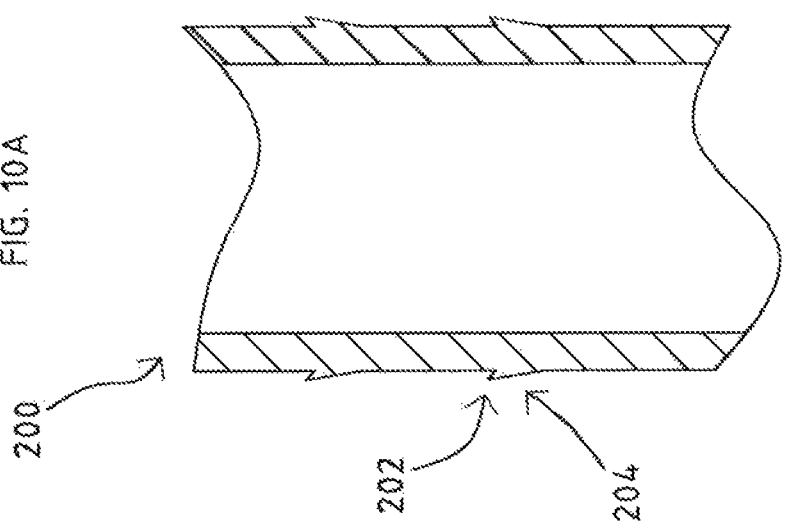

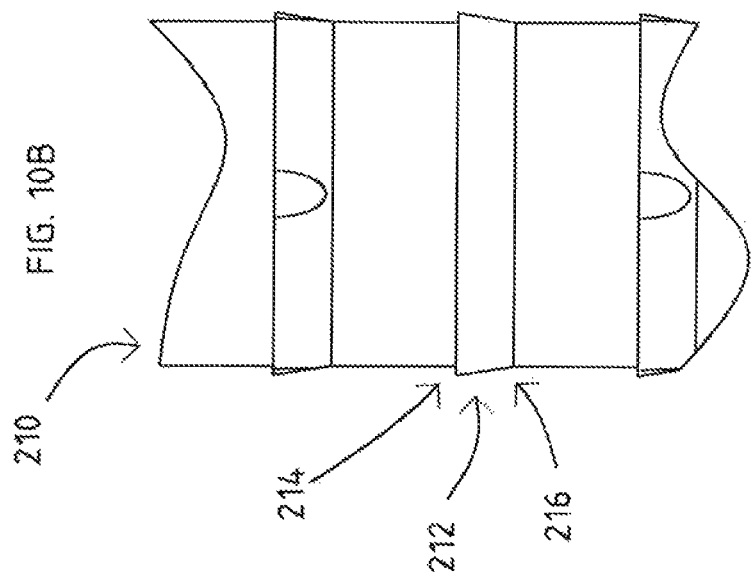
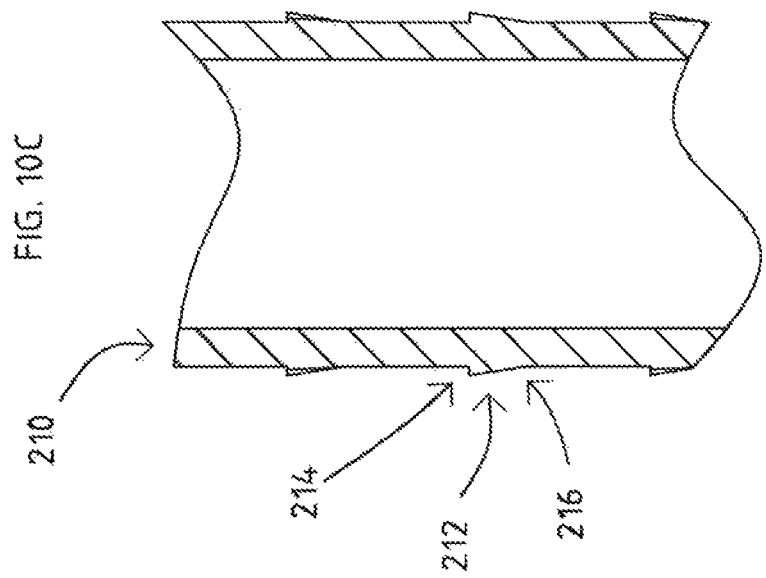

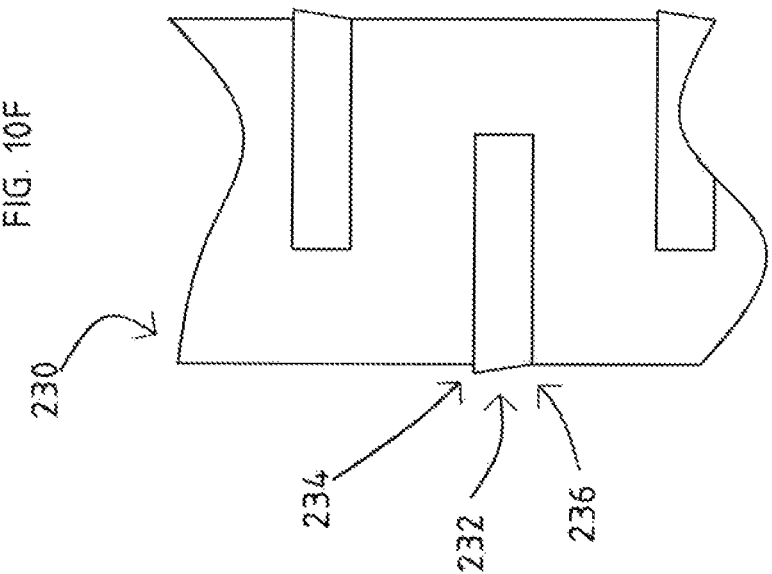
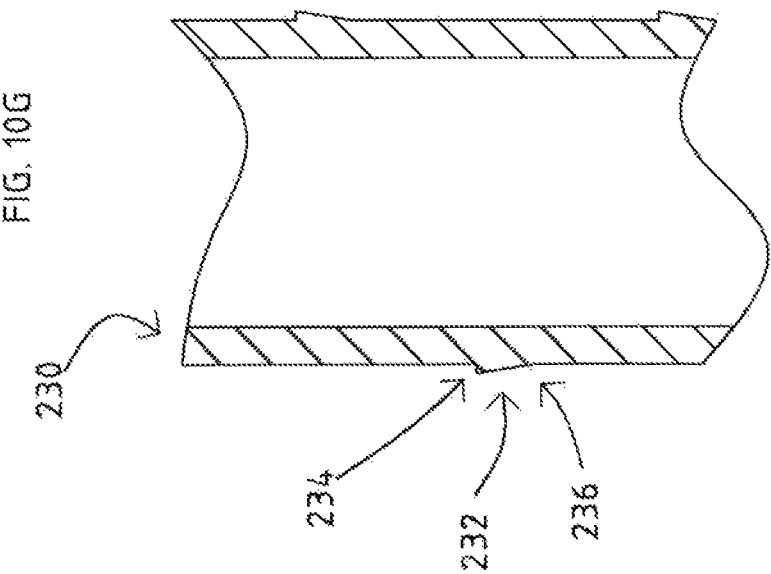

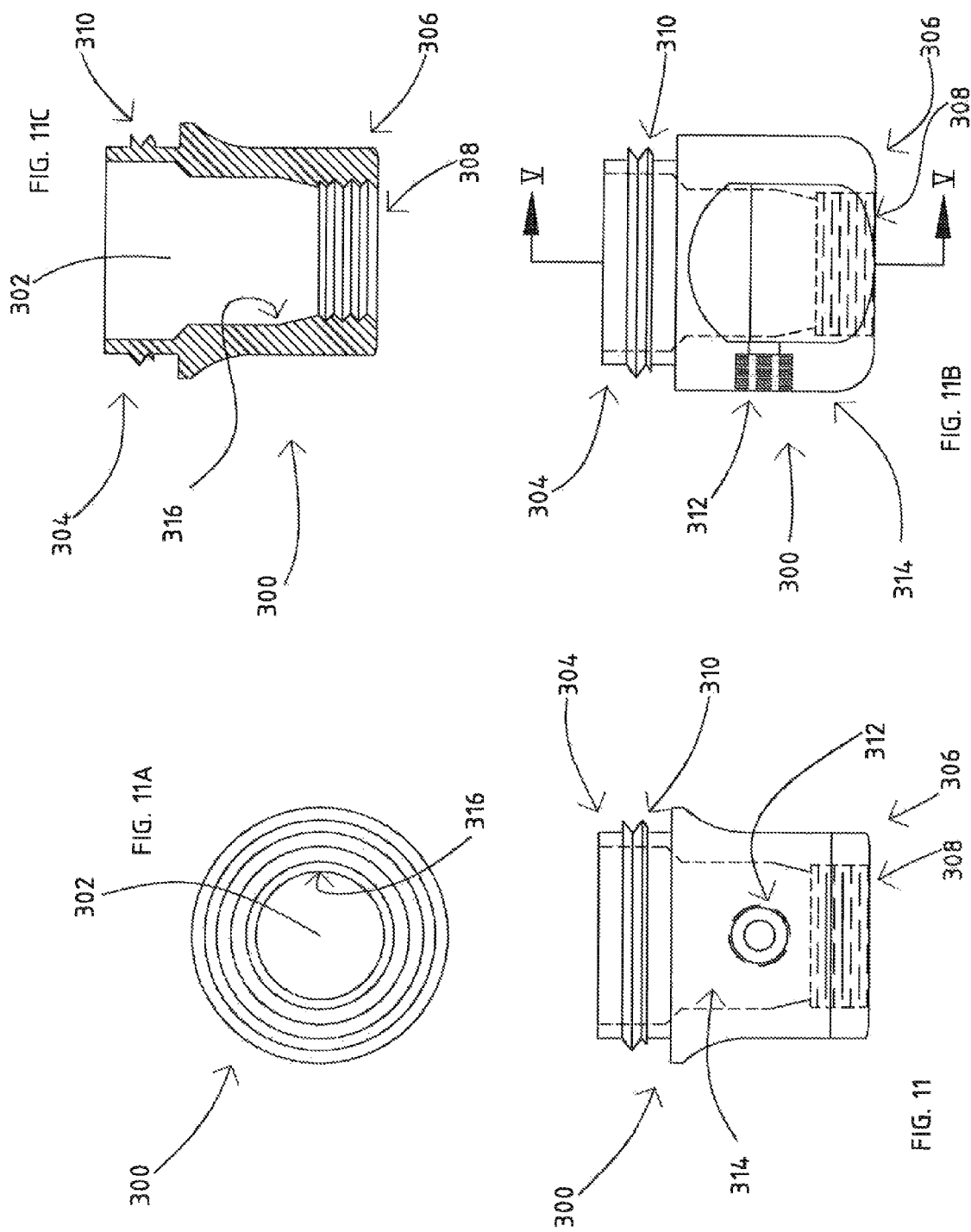

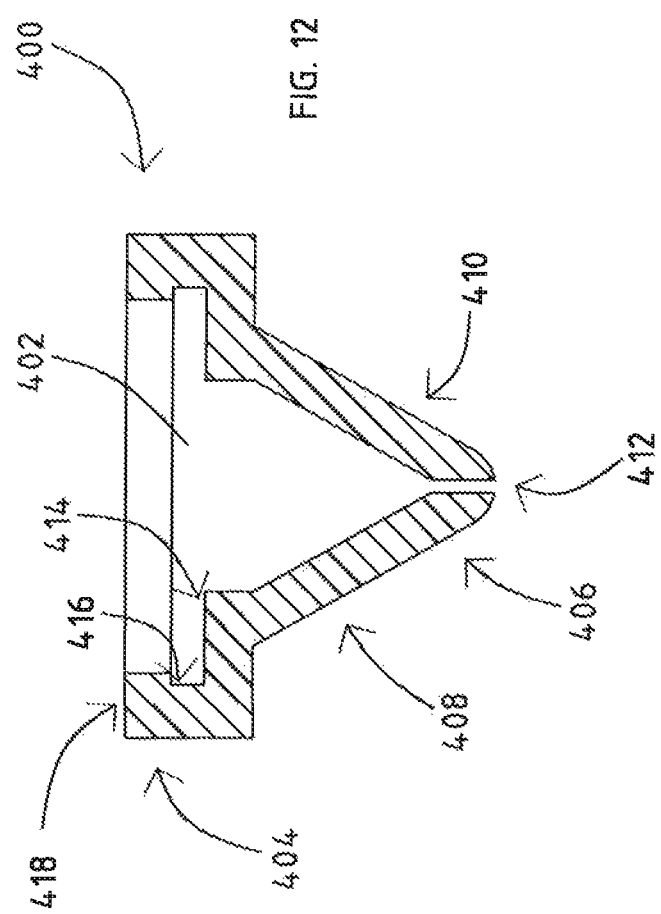

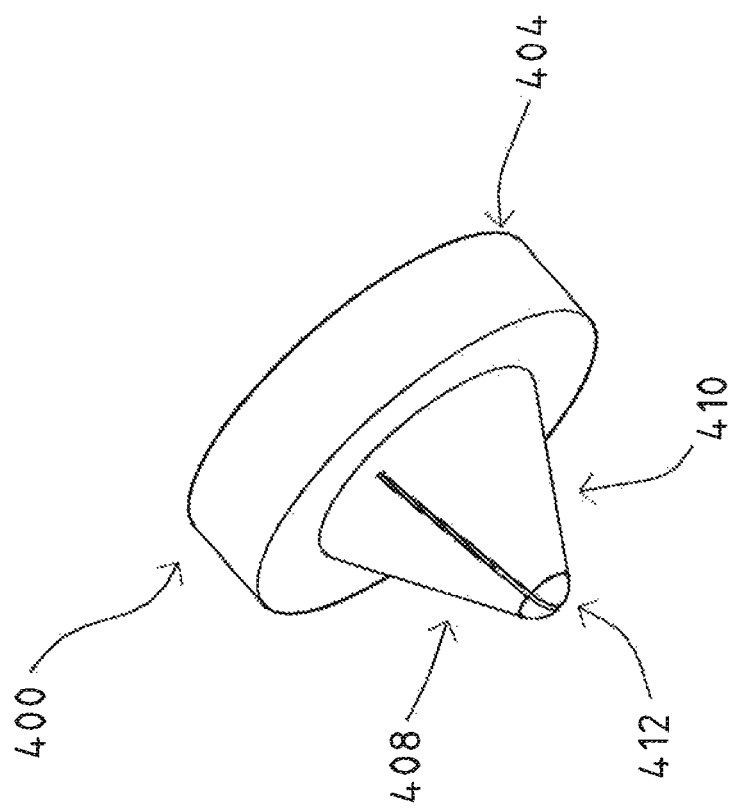

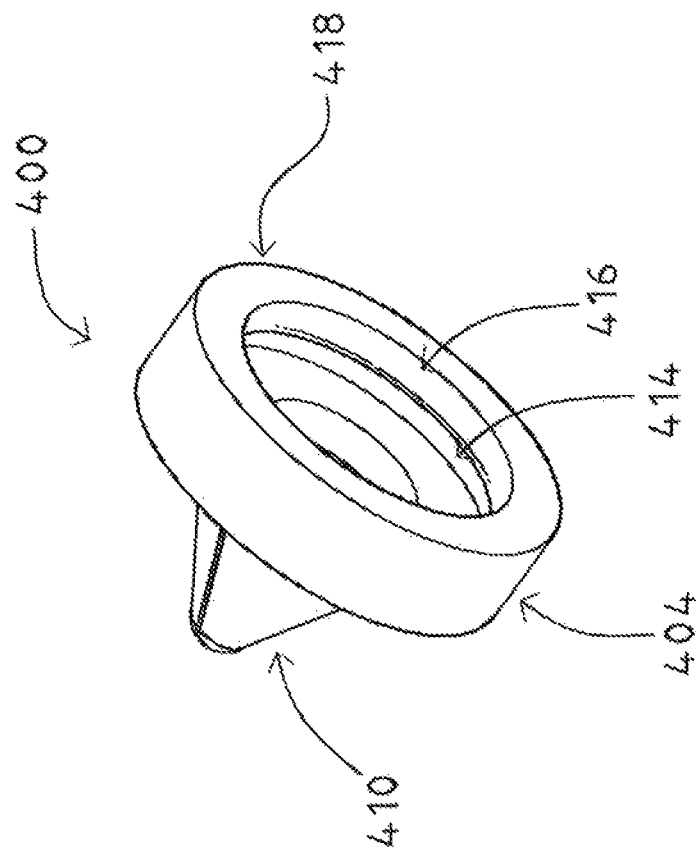

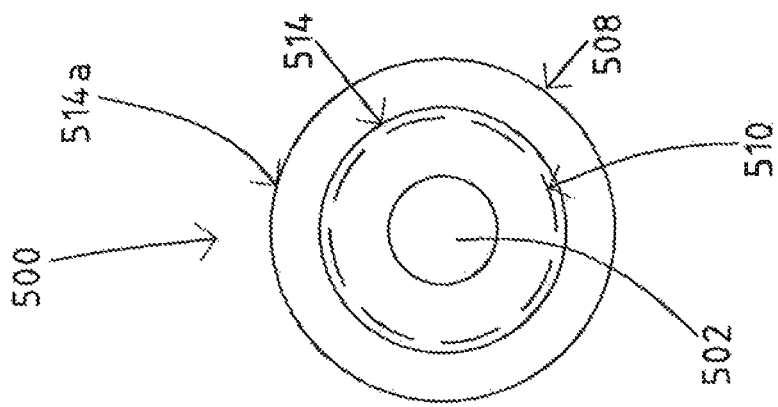
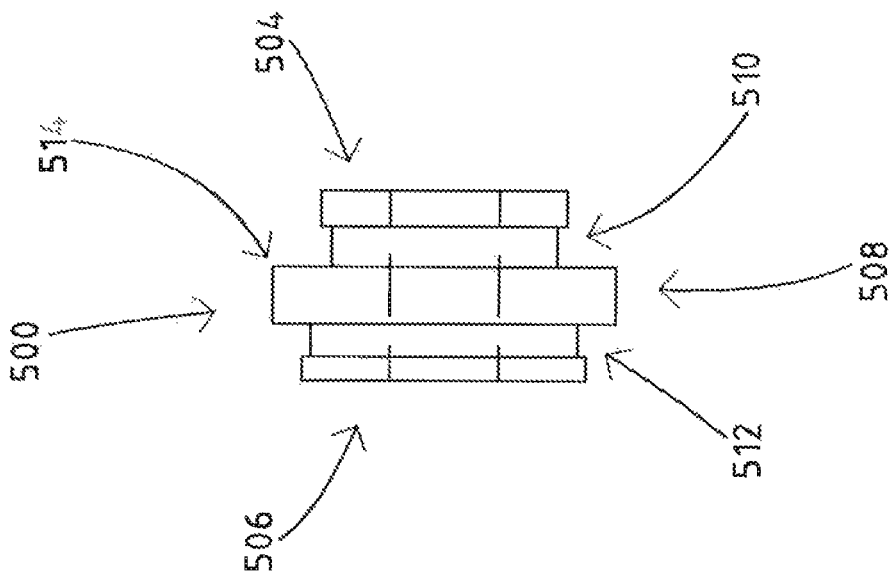
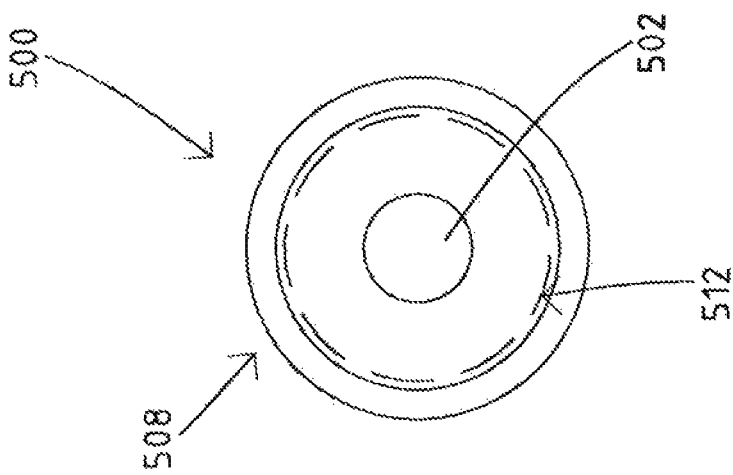

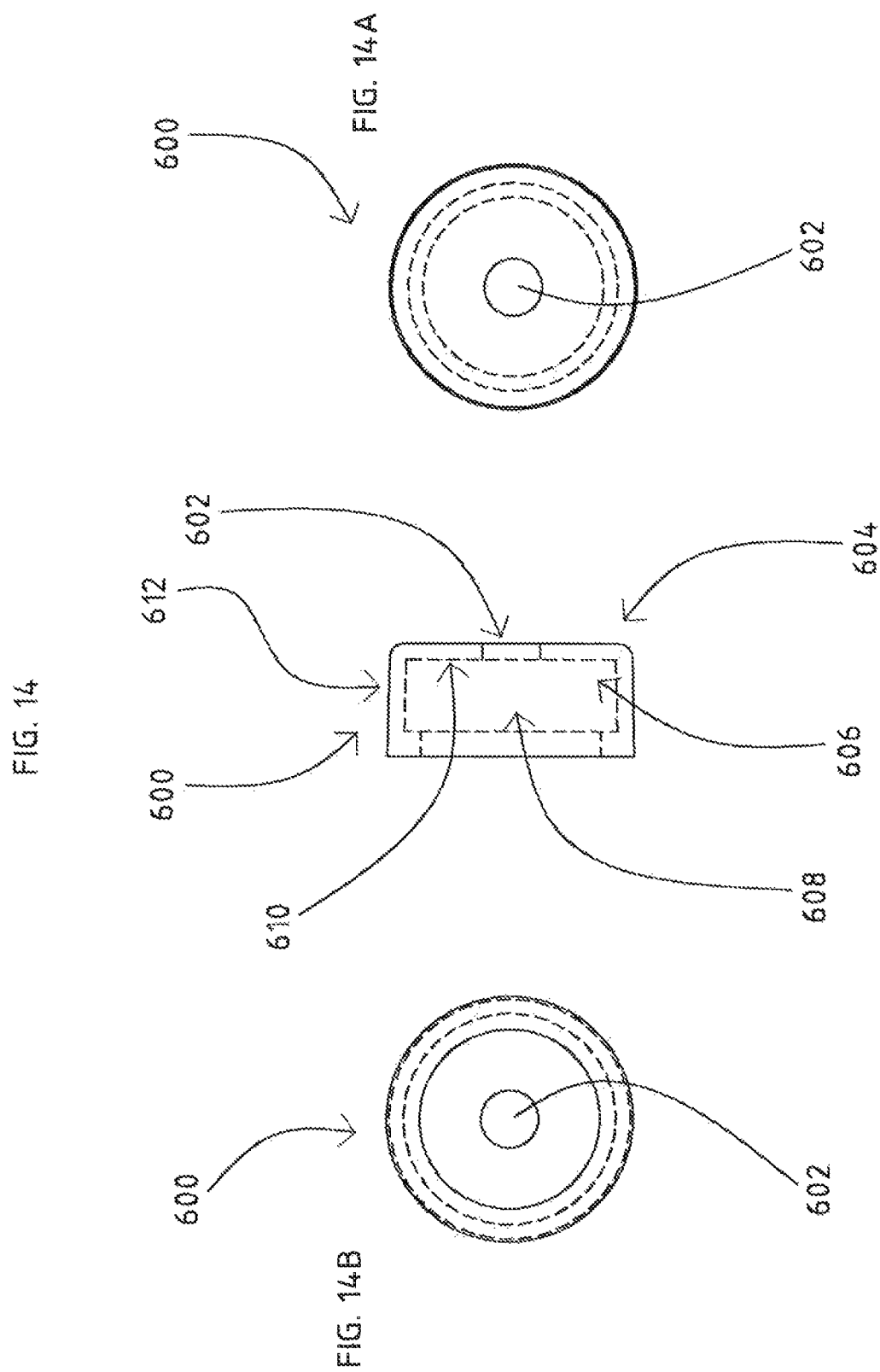

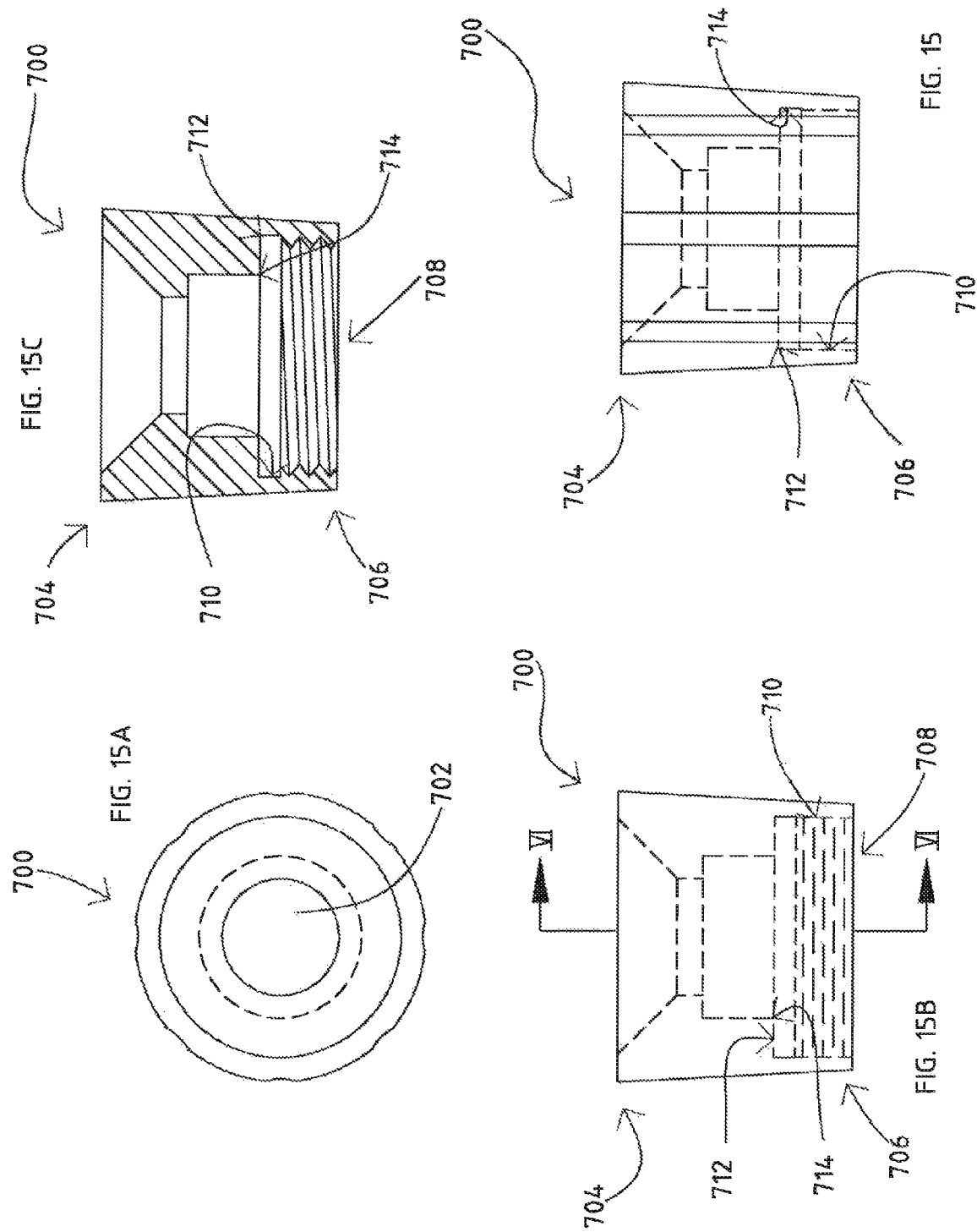

CANNULA SYSTEM

CROSS-REFERENCE TO RELATED APPLICATION

The instant application claims priority to U.S. Provisional Patent Application Ser. No. 61/412,553, filed Nov. 11, 2010, the entire specification of which is expressly incorporated herein by reference.

FIELD OF INVENTION

The present invention relates generally to cannulas and more specifically to reposable and/or reusable cannula systems.

BACKGROUND OF THE INVENTION

Endoscopy, and especially laparoscopic endoscopy, has been a rapidly growing surgical practice in the past decades. Accessing the patient's laparoscopic cavity is typically done via holes, usually punctured with a sharp element referred to as a trocar. In order to penetrate the patient's laparoscopic cavity, the trocar is placed into a tubular element referred to as a cannula, such that the sharp end of the trocar is protruding from the cannula's distal end. Once the trocar end punctures the abdominal wall and enters the body cavity, it can be withdrawn and various surgical instruments may then be introduced through the cannula and into the body cavity.

Cannulas are most commonly a single patient use instrument, although there is greater interest in developing reposable (i.e., suitable for a relatively low number of surgical uses) and/or reusable (i.e., suitable for a relatively high number of surgical uses) cannulas that can be appropriately sterilized again and again for use with multiple numbers of patients. Attempts to design and/or manufacture conventional cannula systems that are reposable and/or reusable have not been entirely satisfactory.

Accordingly, there exists a need for new and improved reusable cannula systems that overcome at least one of the aforementioned disadvantages.

SUMMARY OF THE INVENTION

In accordance with the general teachings of the present invention, a new and improved cannula system is provided. The cannula system allows for penetration of an associated trocar into the patient's abdominal cavity. The cannula system may be formed of biocompatible materials that are suitable to be sterilized numerous times. Accordingly, the cannula system may be reusable for a relatively large number of surgical procedures assuming conventional sterilization techniques are employed after each surgical procedure. Additionally, the cannula system may be provided with an internal valve system disposed in a port portion thereof wherein the valve system may be operable to receive the trocar there through, as well as maintaining insufflation of the body cavity. Furthermore, the cannula system may be provided with a plurality of rib members formed on an external surface of the cannula shaft, wherein the rib members may engage the tissues adjacent the incision hole, thus maintaining the position of the cannula shaft and reducing and/or lessening relative movement of the cannula shaft.

In accordance with an embodiment of the present invention, a cannula system is provided, comprising: a cannula member having a proximal portion and a distal portion, wherein the cannula member includes an area defining a through bore extending from the proximal portion to the distal portion; a port member having a proximal portion and a distal portion, wherein the port member includes an area defining a through bore extending from the proximal portion to the distal portion, wherein the distal portion of the port member is operable to be at least partially received within the proximal portion of the cannula member; a valve member having a proximal portion and a distal portion, wherein the valve member is operable to be at least partially received within the proximal portion of the port member; a retainer member having a proximal portion and a distal portion, wherein the retainer member includes an area defining a through bore extending from the proximal portion to the distal portion, wherein the distal portion of the retainer member is operable to be at least partially received within the proximal portion of the valve member, wherein a surface of the distal portion of the retainer member is operable to releasably engage a surface of the proximal portion of the valve member; and a seal member, wherein the seal member includes an area defining a bore formed in a surface thereof, wherein the seal member is operable to envelop the proximal portion of the retainer, wherein a surface of the seal member is operable to releasably engage a surface of the proximal portion of the retainer member.

In accordance with an aspect of this embodiment, a cap member is provided having a proximal portion and a distal portion, wherein the cap member includes an area defining a through bore extending from the proximal portion to the distal portion, wherein a surface of the distal portion of the cap member is operable to releasably engage a surface of the proximal portion of the port member.

In accordance with an aspect of this embodiment, any of the cannula member, port member, valve member, retainer member, seal member, and cap member is comprised of a reusable and/or reposable material.

In accordance with an aspect of this embodiment, any of the cannula member, port member, retainer member, and cap member is comprised of a thermoplastic material.

In accordance with an aspect of this embodiment, any of the valve member and seal member is comprised of a rubber material.

In accordance with an aspect of this embodiment, the cannula member has a smooth external surface.

In accordance with an aspect of this embodiment, the cannula member has a plurality of ribbed members disposed on an external surface thereof.

In accordance with an aspect of this embodiment, none of the rib members contact an adjacent rib member.

In accordance with an aspect of this embodiment, at least one rib member extends continuously around the circumference of the cannula member.

In accordance with an aspect of this embodiment, at least one rib member does not extend continuously around the circumference of the cannula member.

In accordance with an aspect of this embodiment, at least one rib member includes a planar surface extending outwardly away from the external surface of the cannula member and a tapered surface extending inwardly towards the external surface of the cannula member.

In accordance with an aspect of this embodiment, at least one rib member includes at least one area defining an indentation formed in a surface thereof.

In accordance with an aspect of this embodiment, at least one rib member includes a rounded surface profile.

In accordance with an aspect of this embodiment, at least one rib member includes an outwardly beveled surface profile.

In accordance with an aspect of this embodiment, at least one rib member includes a raised planar surface profile.

In accordance with an aspect of this embodiment, at least one rib member includes a chevron-shaped surface profile.

In accordance with an aspect of this embodiment, at least one rib member includes an inwardly beveled surface profile.

In accordance with an aspect of this embodiment, the valve member is a duckbill type valve.

In accordance with an alternative embodiment of the present invention, a cannula system is provided, comprising: a cannula member having a proximal portion and a distal portion, wherein the cannula member includes an area defining a through bore extending from the proximal portion to the distal portion, a port member having a proximal portion and a distal portion, wherein the port member includes an area defining a through bore extending from the proximal portion to the distal portion, wherein the distal portion of the port member is operable to be at least partially received within the proximal portion of the cannula member, a valve member having a proximal portion and a distal portion, wherein the valve member is operable to be at least partially received within the proximal portion of the port member, a retainer member having a proximal portion and a distal portion, wherein the retainer member includes an area defining a through bore extending from the proximal portion to the distal portion, wherein the distal portion of the retainer member is operable to be at least partially received within the proximal portion of the valve member, wherein an annular flange member of the distal portion of the retainer member is operable to releasably engage an area defining a groove formed on a surface of the proximal portion of the valve member, and a seal member, wherein the seal member includes an area defining a bore formed in a surface thereof, wherein the seal member is operable to envelop the proximal portion of the retainer, wherein an annular flange member of the seal member is operable to releasably engage an area defining a groove formed on a surface of the proximal portion of the retainer member.

In accordance with an aspect of this embodiment, a cap member is provided having a proximal portion and a distal portion, wherein the cap member includes an area defining a through bore extending from the proximal portion to the distal portion, wherein a threaded surface of the distal portion of the cap member is operable to releasably engage a threaded surface of the proximal portion of the port member.

Further areas of applicability of the present invention will become apparent from the detailed description provided hereinafter. It should be understood that the detailed description and specific examples, while indicating the preferred embodiment of the invention, are intended for purposed of illustration only and are not intended to limit the scope of the invention.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 illustrates an exploded view of a cannula system, in accordance with a first embodiment of the present invention;

FIG. 1A illustrates a cutaway view of a valve assembly, in accordance with a second embodiment of the present invention;

FIG. 1B illustrates a cutaway view of a valve assembly seated in a port member, in accordance with a third embodiment of the present invention;

FIG. 1D illustrates a cutaway view of a valve assembly seated in a port member that is in turn seated in a head portion of a cannula, wherein a cap member is secured to the head portion, in accordance with a fifth embodiment of the present invention;

FIG. 2 illustrates an elevational view of a cannula system, in accordance with a sixth embodiment of the present invention;

FIG. 3 illustrates an elevational view of a cannula member having a smooth external surface, in accordance with a seventh embodiment of the present invention;

FIG. 3A illustrates a top plan view of the cannula member depicted in FIG. 3, in accordance with an eighth embodiment of the present invention;

FIG. 3B illustrates a partial detail view of the proximal portion of the cannula member depicted in FIG. 3, in accordance with a ninth embodiment of the present invention;

FIG. 3C illustrates a partial detail view of the distal portion of the cannula member depicted in FIG. 3, in accordance with a tenth embodiment of the present invention;

FIG. 4 illustrates an elevational view of a cannula member having a ribbed external surface, in accordance with an eleventh embodiment of the present invention;

FIG. 4A illustrates a top plan view of the cannula member depicted in FIG. 4, in accordance with a twelfth embodiment of the present invention;

FIG. 4B illustrates a partial detail view of the proximal portion of the cannula member depicted in FIG. 4, in accordance with a thirteenth embodiment of the present invention;

FIG. 4C illustrates a partial detail view of the distal portion of the cannula member depicted in FIG. 4, in accordance with a fourteenth embodiment of the present invention;

FIG. 4D illustrates a sectional view taken along line I-I of FIG. 4, in accordance with a fifteenth embodiment of the present invention;

FIG. 5 illustrates a perspective view of a cannula member having a ribbed external surface, in accordance with a sixteenth embodiment of the present invention;

FIG. 7 illustrates an elevational view of a cannula member having a discontinuous ribbed external surface, in accordance with an eighteenth embodiment of the present invention;

FIG. 7A illustrates a sectional view taken along line II-II of FIG. 7, in accordance with a nineteenth embodiment of the present invention;

FIG. 8 illustrates an elevational view of a cannula member having an alternative discontinuous ribbed external surface, in accordance with a twentieth embodiment of the present invention;

FIG. 8A illustrates a sectional view taken along line III-III of FIG. 8, in accordance with a twenty-first embodiment of the present invention;

FIG. 8B illustrates an elevational view of a cannula member having an non-ribbed external surface, in accordance with a twenty-second embodiment of the present invention;

FIG. 8C illustrates a sectional view taken along line Iv-Iv of FIG. 8B, in accordance with a twenty-third embodiment of the present invention;

FIG. 9 illustrates a partial elevational view of a cannula member having a ribbed external surface, in accordance with a twenty-fourth embodiment of the present invention;

FIG. 9A illustrates a partial cross-sectional view of the cannula member depicted in FIG. 9, in accordance with a twenty-fifth embodiment of the present invention;

FIG. 10 illustrates a partial elevational view of a fourth alternative cannula member having a continuous or discontinuous ribbed external surface, in accordance with a thirty-second embodiment of the present invention;

FIG. 10A illustrates a partial cross-sectional view of the cannula member depicted in FIG. 10, in accordance with a thirty-third embodiment of the present invention;

FIG. 10B illustrates a partial elevational view of a fifth alternative cannula member having a continuous or discontinuous ribbed external surface, in accordance with a thirty-fourth embodiment of the present invention;

FIG. 10C illustrates a partial cross-sectional view of the cannula member depicted in FIG. 10B, in accordance with a thirty-fifth embodiment of the present invention;

FIG. 10F illustrates a partial elevational view of a seventh alternative cannula member having a continuous or discontinuous ribbed external surface, in accordance with a thirty-eighth embodiment of the present invention;

FIG. 10G illustrates a partial cross-sectional view of the cannula member depicted in FIG. 10F, in accordance with a thirty-ninth embodiment of the present invention;

FIG. 11 illustrates an elevational view of a port member of a cannula system, in accordance with a fortieth embodiment of the present invention;

FIG. 11A illustrates a top plan view of a port member of a cannula system, in accordance with a forty-first embodiment of the present invention;

FIG. 11B illustrates a partial broken away elevational view of a port member of a cannula system, in accordance with a forty-second embodiment of the present invention;

FIG. 11C illustrates a sectional view taken along line V-V of FIG. 11B, in accordance with a forty-third embodiment of the present invention;

FIG. 12 illustrates a cross-sectional view of a valve member of a cannula system, in accordance with a forty-fourth embodiment of the present invention;

FIG. 12A is a bottom perspective view of a valve member of a cannula system. In accordance with a forty-fifth embodiment of the present invention;

FIG. 12B is a top perspective view of a valve member of a cannula system. In accordance with a forty-sixth embodiment of the present invention;

FIG. 13 illustrates a side view of a retainer member of a cannula system, in accordance with a forty-seventh embodiment of the present invention;

FIG. 13A illustrates a top plan view of a retainer member of a cannula system, in accordance with a forty-eighth embodiment of the present invention;

FIG. 13B illustrates a bottom plan view of a retainer member of a cannula system, in accordance with a forty-ninth embodiment of the present invention;

FIG. 14 illustrates a side view of a seal member of a cannula system, in accordance with a fiftieth embodiment of the present invention;

FIG. 14A illustrates a top plan view of a seal member of a cannula system, in accordance with a fifty-first embodiment of the present invention;

FIG. 14B illustrates a bottom plan view of a seal member of a cannula system, in accordance with a fifty-second embodiment of the present invention;

FIG. 15 illustrates an elevational view of a cap member of a cannula system, in accordance with a fifty-third embodiment of the present invention;

FIG. 15A illustrates a top plan view of a cap member of a cannula system, in accordance with a fifty-fourth embodiment of the present invention;

FIG. 15B illustrates another elevational view of a cap member of a cannula system, in accordance with a fifty-fifth embodiment of the present invention; and FIG. 15C illustrates a sectional view taken along line VI-VI of FIG. 15B, in accordance with a fifty-sixth embodiment of the present invention.

The same reference numerals refer to the same parts throughout the various Figures.

DETAILED DESCRIPTION OF THE INVENTION

The following description of the preferred embodiment(s) is merely exemplary in nature and is in no way intended to limit the invention, or uses.

Figure 1C:
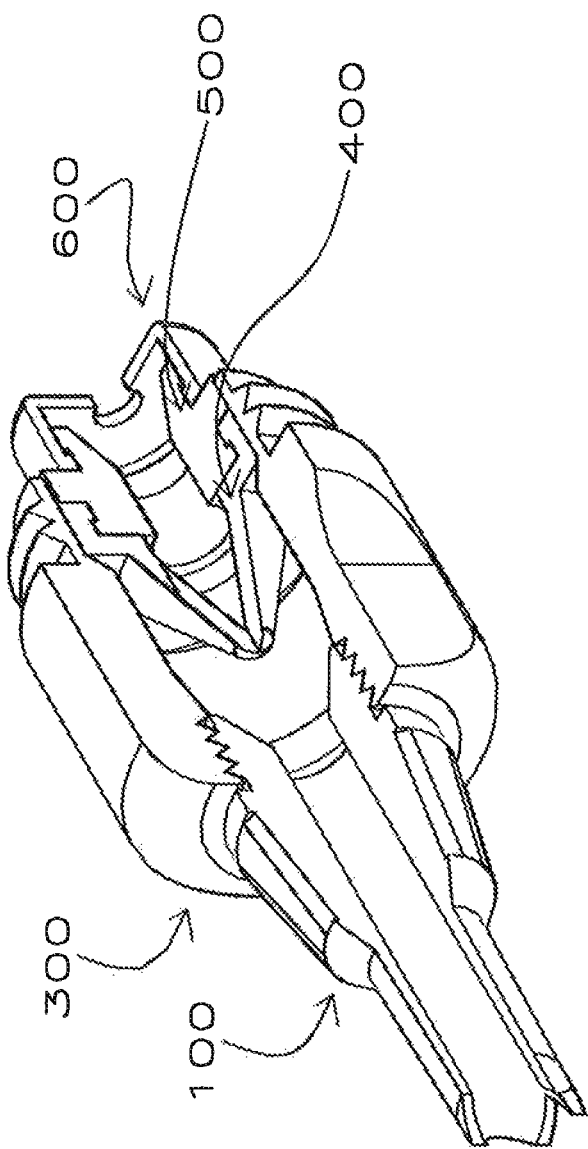
FIG. 1C illustrates a cutaway view of a valve assembly seated in a port member that is in turn seated in a head portion of a cannula, in accordance with a fourth embodiment of the present invention.

Referring to the Figures generally, and specifically to FIGS. 1-2, there is shown a cannula system generally at 10. The cannula system 10 primarily includes a cannula member 100, a port member 300, a valve member 400, a retainer member 500, a seal member 600 and a cap member 700. It should be appreciated that the cannula system 10 of the present invention is operable to interoperate with a trocar or similar device during a surgical procedure.

The cannula member 100 may be comprised of a biocompatible material. By way of a non-limiting example, the cannula member 100 may be comprised of thermoplastics, such as but not limited to polyphenylsulfone, such as but not limited to RADEL® R-5500 (Solvay Advanced Polymers L.L.C., Alpharetta Ga.). The chosen material may be suitable to be sterilized by conventional methods numerous times without any appreciable degradation or loss of function.

Referring to FIGS. 3-3C, there is shown various views of the cannula member 100, wherein the cannula member 100 may have a smooth external surface 102. The cannula member 100 may include a proximal head portion 104, a shaft portion 105, and a distal end portion 106. An area defining a lumen or through bore 108 may be formed within an interior portion of the cannula member 100, allowing instrumentation (e.g., a trocar) to be inserted into the head portion 104 and extend through the end portion 106. The head portion 104 may include an external thread portion 110 (the purpose of which will be explained herein). The end portion 106 may include an angled portion 112 for facilitating insertion of the cannula member 100 through the patient's tissue towards the intended body cavity.

Figure 6:
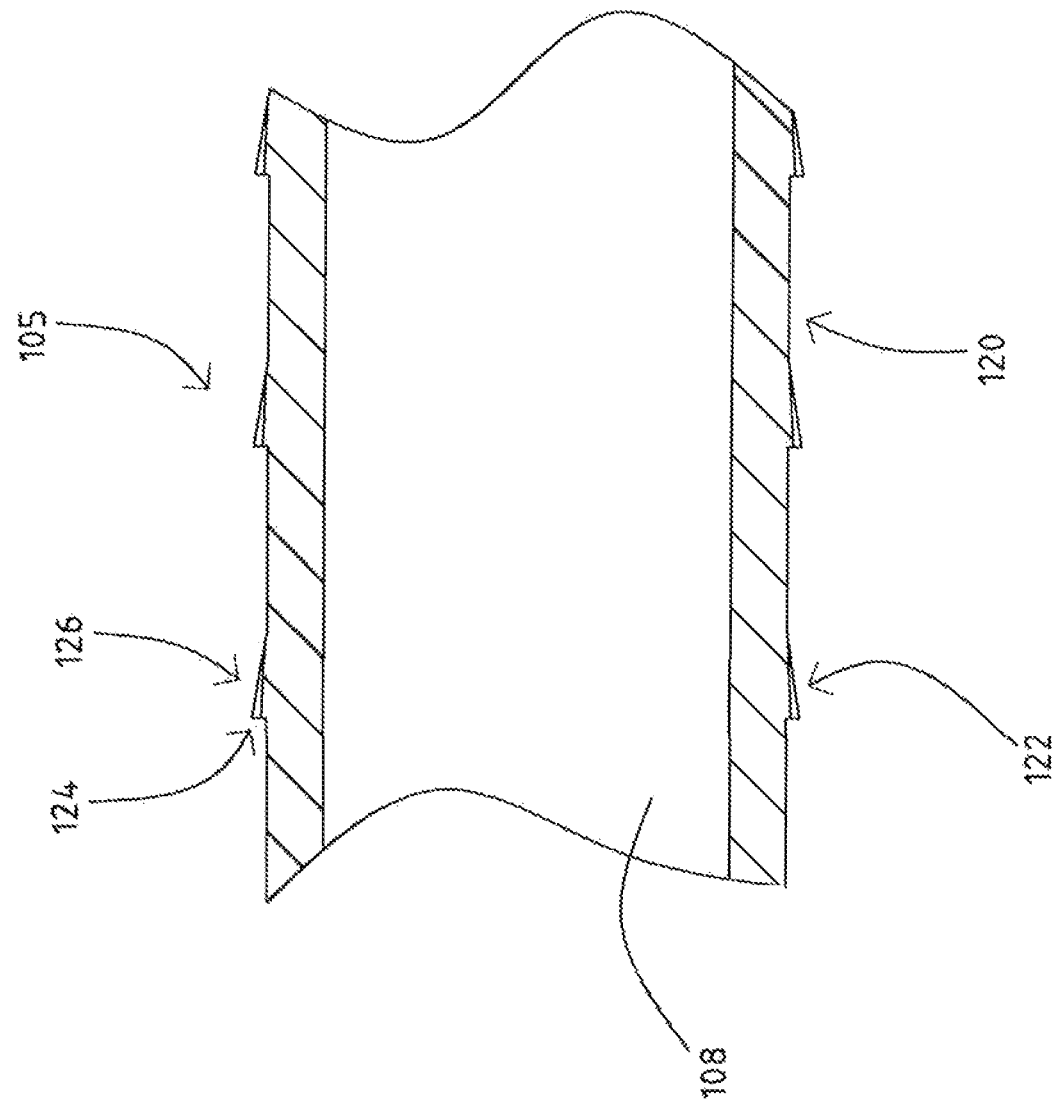
FIG. 6 illustrates a partial cross-sectional view of the cannula member depicted in FIG. 5, in accordance with a seventeenth embodiment of the present invention.

Referring to FIGS. 4-6, there is shown various views of the cannula member 100, wherein the shaft portion 105 of the cannula member 100 may have a ribbed external surface 120 including a plurality of rib members 122 formed thereon. By way of a non-limiting example, the rib members 122 may aid in engaging the tissues adjacent the incision hole, thus maintaining the position of the shaft portion 105 and reducing and/or lessening relative movement of the shaft portion 105.

In these views, each of the rib members 122 may extend outwardly from the external surface 102. By way of a non-limiting example, the rib members 122 may include a planar surface 124 and a tapered surface 126 extending back towards the external surface 102 (e.g., see FIG. 6). However, it should be noted that no portion of the ribbed members 122 contact one another, i.e., adjacent rib members 122 do not contact each other. Additionally, as shown, for example, in FIGS. 4, 4B and 4D, the head portion 104 may be provided with a plurality of fluted or scalloped portions 124a formed on the external surface thereof to aid in gripping the head portion 104, e.g., by the surgeon.

Referring to FIGS. 7-7A, there are shown various views of the cannula member 100, wherein the rib members 122 may include at least one, and preferably, at least two areas defining indentations or discontinuities 130 formed along the outer circumference of the rib members 122. In this view, the indentations or discontinuities 130 may be spaced and opposed from one another, although it is envisioned that the relative placement of the indentations or discontinuities 130 may be varied. By way of a non-limiting example, the indentations or discontinuities 130 may further aid in engaging the tissues adjacent the incision hole, thus maintaining the position of the shaft portion 105 and reducing and/or lessening relative movement of the shaft portion 105.

Referring to FIGS. 8-8A, there are shown various views of the cannula member 100, wherein the rib members 122 may include at least one, and preferably, at least four areas defining indentations or discontinuities 140 formed along the outer circumference of the rib members 122. In this view, the indentations or discontinuities 140 may be equally spaced and opposed from one another, although it is envisioned that the relative placement of the indentations or discontinuities 140 may be varied. By way of a non-limiting example, the indentations or discontinuities 140 may further aid in engaging the tissues adjacent the incision hole, thus maintaining the position of the shaft portion 105 and reducing and/or lessening relative movement of the shaft portion 105.

Referring to FIGS. 8B-8C, there are shown various views of the cannula member 100, wherein the rib members 122 do not include any areas defining indentations or discontinuities formed along the outer circumference of the rib members 122.

Figure 9B:
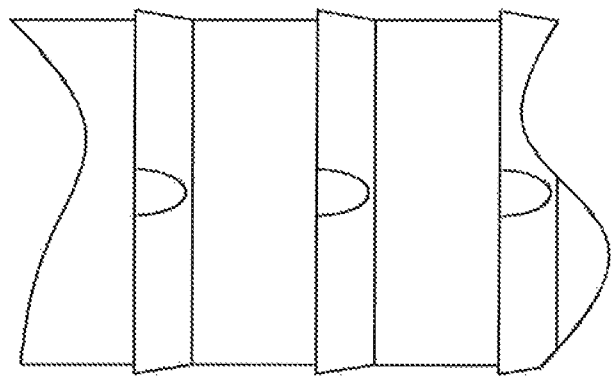
FIG. 9B illustrates a partial elevational view of a first alternative cannula member having a ribbed external surface, in accordance with a twenty-sixth embodiment of the present invention.
Figure 9C:
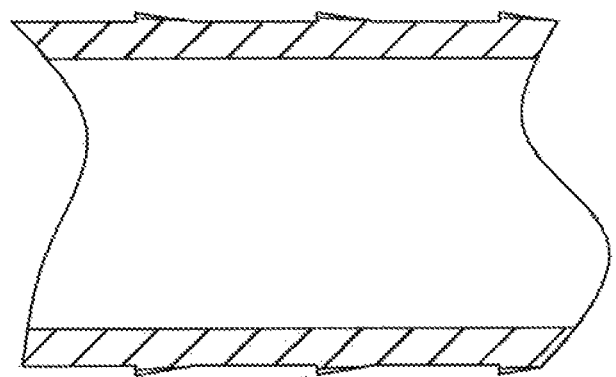
FIG. 9C illustrates a partial cross-sectional view of the cannula member depicted in FIG. 9B, in accordance with a twenty-seventh embodiment of the present invention.
Figure 9D:
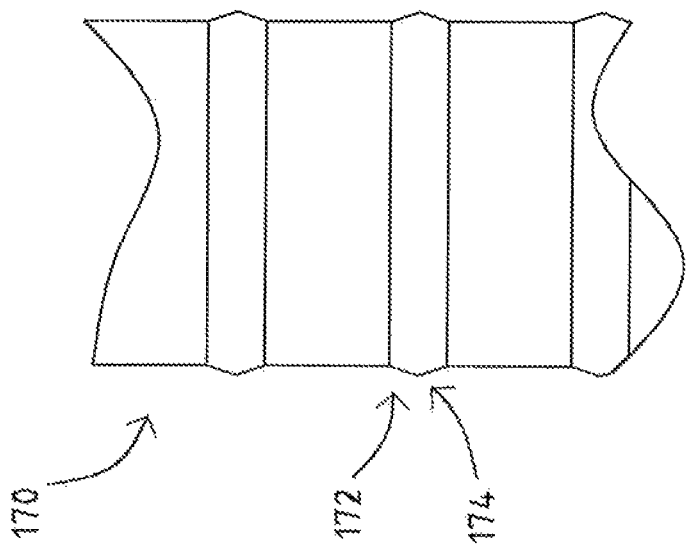
FIG. 9D illustrates a partial elevational view of a second alternative cannula member having a ribbed external surface, in accordance with a twenty-eighth embodiment of the present invention.
Figure 9E:
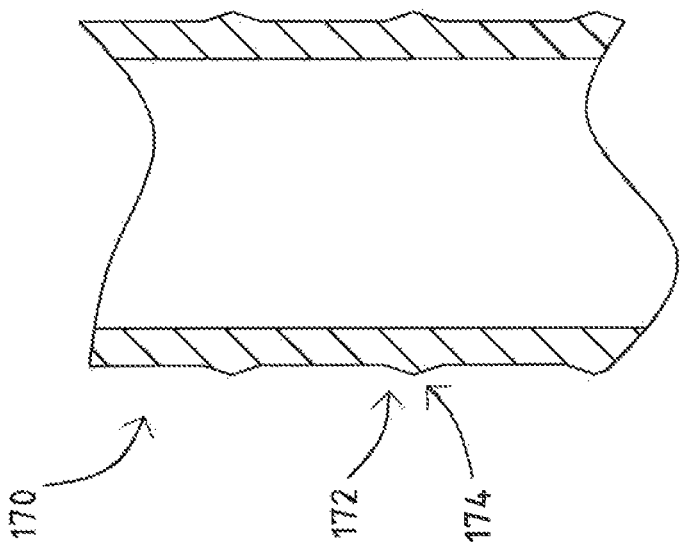
FIG. 9E illustrates a partial cross-sectional view of the cannula member depicted in FIG. 9D, in accordance with a twenty-ninth embodiment of the present invention.
Figure 9F:
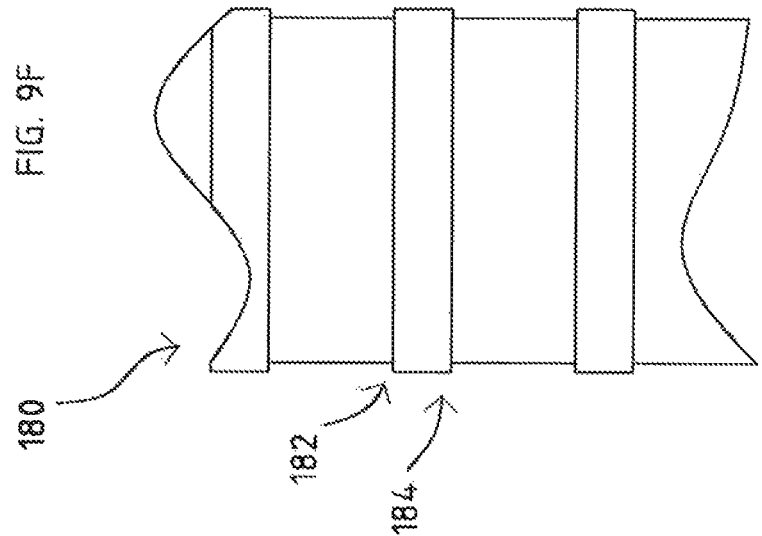
FIG. 9F illustrates a partial elevational view of a third alternative cannula member having a ribbed external surface, in accordance with a thirtieth embodiment of the present invention.
Figure 9G:
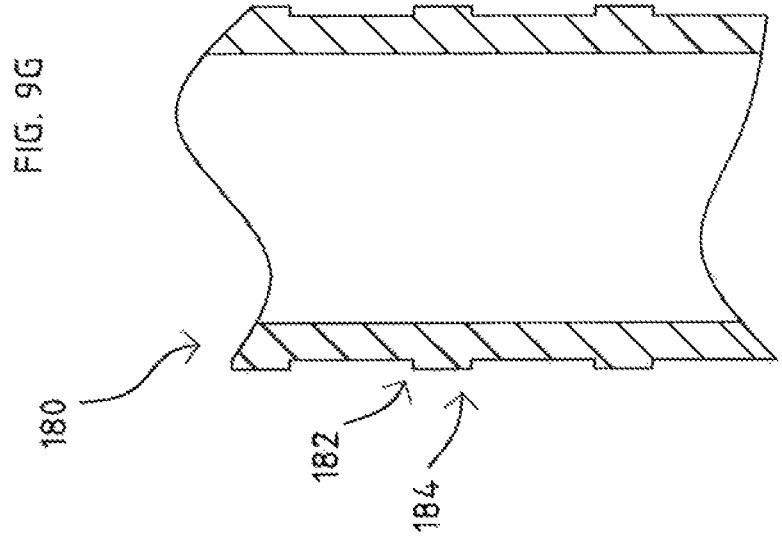
FIG. 9G illustrates a partial cross-sectional view of the cannula member depicted in FIG. 9F, in accordance with a thirty-first embodiment of the present invention.

Referring to FIG. 9-9G, there are shown various views of a cannula member having various configurations of ribbed external surfaces. Referring to FIGS. 9-9A, in system 150, the rib members 152 may be continuous and may possess a rounded profile surface 154. Referring to FIGS. 9B-9C, in system 160, the rib members 162 may be continuous and may include a planar surface 164 and a tapered surface 166. Referring to FIGS. 9D-9E, in system 170, the rib members 172 may be continuous and may include an outwardly extending beveled surface 174. Referring to FIGS. 9F-9G, in system 180, the rib members 182 may be continuous and may include a raised planar surface 184.

Figure 10D:
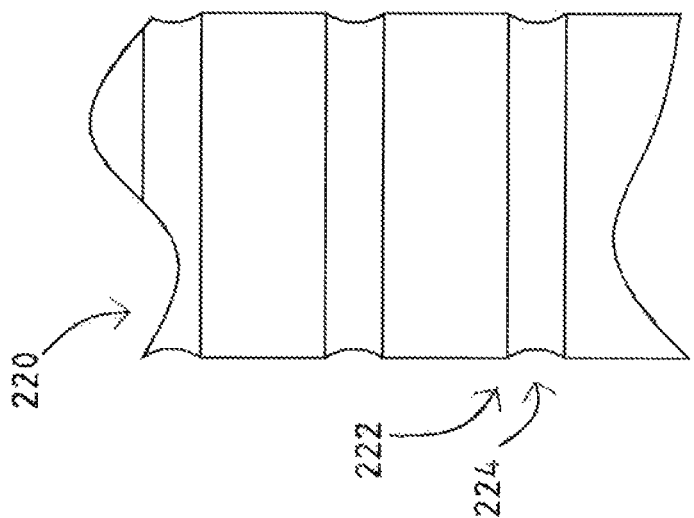
FIG. 10D illustrates a partial elevational view of a sixth alternative cannula member having a continuous or discontinuous ribbed external surface, in accordance with a thirty-sixth embodiment of the present invention.
Figure 10E:
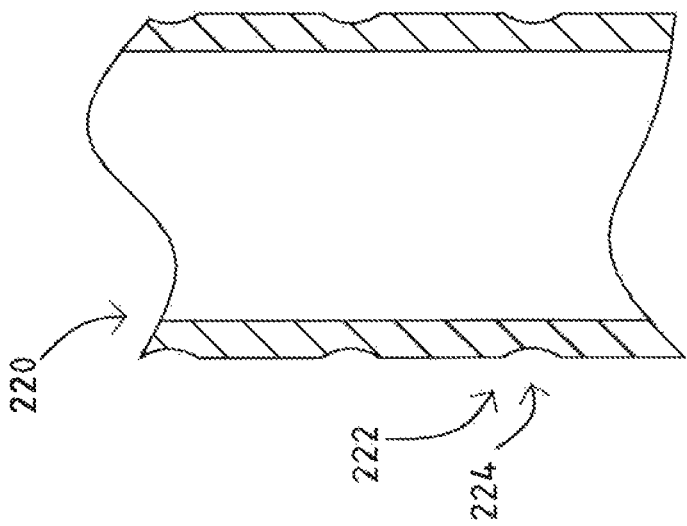
FIG. 10E illustrates a partial cross-sectional view of the cannula member depicted in FIG. 10D, in accordance with a thirty-seventh embodiment of the present invention.

Referring to FIG. 10-10G, there are shown various views of a cannula member having various additional configurations of ribbed external surfaces. Referring to FIGS. 10-10A, in system 200, the rib members 202 may be continuous and may possess a chevron-shaped profile surface 204. Referring to FIGS. 10B-10C, in system 210, the rib members 212 may be continuous and alternating rib members 212 may include a planar surface 214 and a tapered surface 216. Referring to FIGS. 10D-10E, in system 220, the rib members 222 may be continuous and may include an inwardly extending beveled surface 224. Referring to FIGS. 10E-10G, in system 230, the rib members 232 may be discontinuous and may include a planar surface 234 and a tapered surface 236.

Referring to FIGS. 11-11C, there are shown various views of a port member 300 of the cannula system 10. The port member 300 may include an area defining a through bore 302 extending from a proximal portion 304 to a distal portion 306. The through bore 302 may allow instrumentation (e.g., a trocar) to pass there through. The distal portion 306 may include a threaded portion 308 formed on an internal surface 310 thereof. The threaded portion 308 may be intended to threadingly mate with the external thread portion 110 of the cannula member 100. In this manner, the cannula member 100 may be selectively mated to the port member 300. The proximal portion 304 may include an external threaded portion 310 formed thereon (the purpose of which will be described herein). A port passage 312 may be formed on an external surface 314 and may extend to an internal surface 316 of the port member 300. By way of a non-limiting example, the intended purpose of the port passage 312 is to permit an insufflation gas (or other fluid) to be introduced into the body cavity, e.g., via the cannula member 100. It should be appreciated that a stopcock (or other valve system) (not shown) may be operably associated with the port passage 312 to control the flow of the insufflation gas.

By way of a non-limiting example, the port member 300 may be comprised of thermoplastics, such as but not limited to polyphenylsulfone, such as but not limited to RADEL® R-5500 (Solvay Advanced Polymers L.L.C., Alpharetta Ga.). The chosen material may be suitable to be sterilized by conventional methods numerous times without any appreciable degradation or loss of function.

Referring to FIGS. 12-12B, there is shown a valve member 400 of the cannula system 10. In this view, the valve member 400 may be configured as a "duckbill-type" although it is envisioned that other configurations of the valve member may be used as well. The valve member 400 may include an area defining a cavity 402 originating at a proximal portion 404 and terminating at a distal portion 406. A pair of flexible valve walls 408, 410, respectively, may be formed at the distal portion 406. The valve walls 408, 410, respectively, may be selectively operable to permit instrumentation (e.g., a trocar) to extend through a space 412 separating the valve walls 408, 410, respectively. A ledge portion 414 may be formed on an internal surface 416 near the proximal portion 404 of the valve member 400, the intended purpose of which will be described herein. The internal surface 416 may form an "overhang" with respect to ledge portion 414.

The valve member 400 may be intended to be at least partially received within the through bore 302 of the port member 300.

By way of a non-limiting example, the valve member 400 may be comprised of a flexible material, such as but not limited to silicone rubber. The chosen material may be suitable to be sterilized by conventional methods numerous times and may be replaced when any appreciable degradation/defect/wear and/or loss of function occurs.

Referring to FIGS. 13-13B, there are shown various views of a retainer member 500 of the cannula system 10. In this view, the retainer member 500 may include an area defining a through bore 502 originating at a proximal portion 504 and terminating at a distal portion 506. The through bore 502 may be selectively operable to permit instrumentation (e.g., a trocar) to extend there through and assists in keeping the trocar centered relative to a central axis of the cannula member 100, the port member 300 and the valve member 400. An external shoulder member 508 may extend along an external surface 510 of the retainer member 500 and define a lower wall or annular flange portion 512, the intended purpose of which will be described herein. The internal surface 510 may form an "overhang" with respect to proximal portion 504.

The retainer member 500 may be intended to be at least partially received within the cavity 402 of the valve member 400. More specifically, the lower wall portion 512 may be intended to rest upon ledge portion 414 of the valve member 400, with the shoulder member 508 resting upon a top surface 418 of the proximal portion 404 of the valve member 400. Additionally, a portion of the lower wall portion 512 may releasably engage (e.g., via a snap fit) the "overhang" or groove formed by the internal surface 416 and the ledge portion 414.

By way of a non-limiting example, the retainer member 500 may be comprised of thermoplastics, such as but not limited to polyphenylsulfone, such as but not limited to RADEL® R-5500 (Solvay Advanced Polymers L.L.C., Alpharetta Ga.). The chosen material may be suitable to be sterilized by conventional methods numerous times without any appreciable degradation or loss of function.

Referring to FIGS. 14-14B, there are shown various views of a seal member 600 of the cannula system 10. In this view, the seal member 600 may include an area defining a through bore 602 originating at a proximal portion 604 and terminating at a distal portion 606. The through bore 602 may be selectively operable to permit instrumentation (e.g., a trocar) to extend there through and assist in keeping the trocar centered relative to a central axis of the cannula member 100, the port member 300, the valve member 400, and the retainer member 500. An area defining a cavity 608 may be formed proximate an underside surface 610 of the seal member 600 and further define an annular wall or flange member 612 extending downwardly away from the distal portion 606. The seal member 600, specifically the wall member 612, may be intended to fit snuggly on top of an upper surface 514 of the shoulder member 508 of the retainer member 500. Additionally, a portion of the annular wall member 612 may releasably engage (e.g., via a snap fit) the "overhang" or groove formed by the internal surface 510 and the proximal portion 504. In this manner, the seal member 600 may prevent, or at least lessen, the escape of any insufflation gas that has been introduced into the port passage 312.

By way of a non-limiting example, the seal member 600 may be comprised of a flexible material, such as but not limited to silicone rubber. The chosen material may be suitable to be sterilized by conventional methods numerous times and can be replaced when any appreciable degradation/defect/wear and/or loss of function occurs.

Referring to FIGS. 15-15C, there are shown various views of a cap member 700 of the cannula system 10. In this view, the cap member 700 may include an area defining a through bore 702 originating at a proximal portion 704 and terminating at a distal portion 706. The through bore 702 may be selectively operable to permit instrumentation (e.g., a trocar) to extend there through and assist in keeping the trocar centered relative to a central axis of the cannula member 100, the port member 300, the valve member 400, the retainer member 500, and the seal member 600. The distal portion 706 may include a threaded portion 708 formed on an internal surface 710 thereof. The threaded portion 708 may be intended to threadingly mate with the external thread portion 308 of the port member 300. In this manner, the cap member 700 may be selectively securely mated to the port member 300, which in turns keeps the valve member 400, the retainer member 500, and the seal member 600 in place and properly aligned therewith. By way of a non-limiting example, when the cap member 700 is engaged to the port member 300, a shoulder surface 712 formed on another internal surface 714 (e.g., above the threaded portion 708) of the cap member 700 may engage an outer periphery portion 514a of the upper surface 514 of the shoulder member 508 of the retainer member 500, thus preventing, or at least lessening, any movement of the valve member 400, the retainer member 500, and the seal member 600.

By way of a non-limiting example, the cap member 700 may be comprised of thermoplastics, such as but not limited to polyphenylsulfone, such as but not limited to RADEL® R-5500 (Solvay Advanced Polymers L.L.C., Alpharetta Ga.). The chosen material may be suitable to be sterilized by conventional methods numerous times without any appreciable degradation or loss of function.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cannula system, comprising:
   a cannula member having a proximal portion and a distal portion, wherein the cannula member includes an area defining a through bore extending from the proximal portion to the distal portion;
   a port member having a proximal portion and a distal portion, wherein the port member includes an area defining a through bore extending from the proximal portion to the distal portion, wherein the distal portion of the port member is operable to threadingly engage and at least partially receive the proximal portion of the cannula member;
   a valve member having a proximal portion and a distal portion, wherein the valve member is operable to be at least partially received within the proximal portion of the port member, wherein the valve member includes an area defining an annular groove formed on an internal surface of a proximal portion thereof;
   a retainer member having a proximal portion and a distal portion, wherein the retainer member includes an area defining a through bore extending from the proximal portion to the distal portion, wherein the distal portion of the retainer member is operable to be at least partially received within the proximal portion of the valve member, wherein the retainer member includes an annular flange member formed on an external surface of a distal portion thereof, wherein the annular flange member of the retainer member is operable to releasably engage and be received in the annular groove of the valve member, wherein the retainer member includes an area defining an annular groove formed on an external portion of a proximal portion thereof; and a seal member, wherein the seal member includes an area defining a bore formed in a surface thereof, wherein the seal member is operable to envelop the proximal portion of the retainer, wherein the seal member includes an annular flange member formed on an internal surface of a distal portion thereof, wherein the annular flange member of the seal member is operable to releasably engage and be received in the annular groove of the retainer member;

wherein, when the annular flange member of the retainer member releasably engages the annular groove of the valve member and the annular flange member of the seal member releasably engages the annular groove of the retainer member, the valve member, retainer member and seal member are held in a fixed relationship to one another.

2. The cannula system according to claim 1, further comprising a cap member having a proximal portion and a distal portion, wherein the cap member includes an area defining a through bore extending from the proximal portion to the distal portion, wherein a surface of the distal portion of the cap member is operable to releasably engage a surface of the proximal portion of the port member.

3. The cannula system according to claim 2, wherein any of the cannula member, port member, valve member, retainer member, seal member, and cap member is comprised of a reusable and/or reposable material.

4. The cannula system according to claim 2, wherein any of the cannula member, port member, retainer member, and cap member is comprised of a thermoplastic material.

5. The cannula system according to claim 2, wherein any of the valve member and seal member is comprised of a rubber material.

6. The cannula system according to claim 1, wherein the cannula member has a smooth external surface.

7. The cannula system according to claim 1, wherein the cannula member has a plurality of ribbed members disposed on an external surface thereof.

8. The cannula system according to claim 7, wherein none of the rib members contact an adjacent rib member.

9. The cannula system according to claim 7, wherein at least one rib member extends continuously around the circumference of the cannula member.

10. The cannula system according to claim 7, wherein at least one rib member does not extend continuously around the circumference of the cannula member.

11. The cannula system according to claim 7, wherein at least one rib member includes a planar surface extending outwardly away from the external surface of the cannula member and a tapered surface extending inwardly towards the external surface of the cannula member.

12. The cannula system according to claim 7, wherein at least one rib member includes at least one area defining an indentation formed in a surface thereof.

13. The cannula system according to claim 7, wherein at least one rib member includes a rounded surface profile.

14. The cannula system according to claim 7, wherein at least one rib member includes an outwardly beveled surface profile.

15. The cannula system according to claim 7, wherein at least one rib member includes a raised planar surface profile.

16. The cannula system according to claim 7, wherein at least one rib member includes a chevron-shaped surface profile.

17. The cannula system according to claim 7, wherein at least one rib member includes an inwardly beveled surface profile.

18. The cannula system according to claim 1, wherein the valve member is a duckbill type valve.

19. A cannula system, comprising:

a cannula member having a proximal portion and a distal portion, wherein the cannula member includes an area defining a through bore extending from the proximal portion to the distal portion;

a port member having a proximal portion and a distal portion, wherein the port member includes an area defining a through bore extending from the proximal portion to the distal portion, wherein the distal portion of the port member is operable to threadingly engage and at least partially receive the proximal portion of the cannula member;

a valve member having a proximal portion and a distal portion, wherein the valve member is operable to be at least partially received within the proximal portion of the port member, wherein the valve member is a duckbill type valve, wherein the valve member includes an area defining an annular groove formed on an internal surface of a proximal portion thereof;

a retainer member having a proximal portion and a distal portion, wherein the retainer member includes an area defining a through bore extending from the proximal portion to the distal portion, wherein the distal portion of the retainer member is operable to be at least partially received within the proximal portion of the valve member, wherein an annular flange member of the distal portion of the retainer member is operable to releasably engage and be received in the groove of the valve member, wherein the retainer member includes an area defining an annular groove formed on an external portion of a proximal portion thereof;

a seal member, wherein the seal member includes an area defining a bore formed in a surface thereof, wherein the seal member is operable to envelop the proximal portion of the retainer, wherein the seal member includes an annular flange member formed on an internal surface of a distal portion thereof, wherein the annular flange member of the seal member is operable to releasably engage and be received in the groove of the retainer member;

wherein, when the annular flange member of the retainer member releasably engages the annular groove of the valve member and the annular flange member of the seal member releasably engages the annular groove of the retainer member, the valve member, retainer member and seal member are held in a fixed relationship to one another; and a cap member having a proximal portion and a distal portion, wherein the cap member includes an area defining a through bore extending from the proximal portion to the distal portion, wherein a threaded surface of the distal portion of the cap member is operable to releasably engage a threaded surface of the proximal portion of the port member.

* * * * *

UNITED STATES PATENT AND TRADEMARK OFFICE
CERTIFICATE OF CORRECTION

| | | |
|---|---|---|
| PATENT NO. | : 9,101,315 B2 | Page 1 of 1 |
| APPLICATION NO. | : 13/294493 | |
| DATED | : August 11, 2015 | |
| INVENTOR(S) | : Winfree et al. | |

It is certified that error appears in the above-identified patent and that said Letters Patent is hereby corrected as shown below:

On the title page, item [73] Delete "Specialty Care" insert --SpecialtyCare--.

Signed and Sealed this
Eighth Day of December, 2015

Michelle K. Lee
*Director of the United States Patent and Trademark Office*